(12) United States Patent
Beyer

(10) Patent No.: US 12,396,760 B2
(45) Date of Patent: Aug. 26, 2025

(54) ORTHOPEDIC IMPLANT KIT

(71) Applicant: Neo Medical SA, La Villette (CH)

(72) Inventor: Morten Beyer, Rødkærsbro (DK)

(73) Assignee: NEO MEDICAL S.A., La Villette (CH)

( * ) Notice: Subject to any disclaimer, the term of this patent is extended or adjusted under 35 U.S.C. 154(b) by 1238 days.

(21) Appl. No.: 17/105,683

(22) Filed: Nov. 27, 2020

(65) Prior Publication Data

US 2021/0077155 A1    Mar. 18, 2021

Related U.S. Application Data

(60) Division of application No. 15/939,338, filed on Mar. 29, 2018, now Pat. No. 10,888,356, which is a continuation of application No. 14/890,631, filed as application No. PCT/IB2014/060979 on Apr. 24, 2014, now Pat. No. 10,058,355.

(30) Foreign Application Priority Data

May 13, 2013   (WO) .................. PCT/IB2013/053892

(51) Int. Cl.
*A61B 17/70* (2006.01)
*A61B 17/88* (2006.01)

(52) U.S. Cl.
CPC ...... *A61B 17/7037* (2013.01); *A61B 17/7002* (2013.01); *A61B 17/7032* (2013.01); *A61B 17/7038* (2013.01); *A61B 17/708* (2013.01); *A61B 17/7085* (2013.01); *A61B 17/7086* (2013.01); *A61B 17/7091* (2013.01); *A61B 17/8875* (2013.01)

(58) Field of Classification Search
CPC ........... A61B 17/7074; A61B 17/7076; A61B 17/708; A61B 17/7082; A61B 17/7083; A61B 17/7085; A61B 17/3439
See application file for complete search history.

(56) References Cited

U.S. PATENT DOCUMENTS

| | | | |
|---|---|---|---|
| 3,650,393 A | 3/1972 | Reiss | |
| 4,834,757 A | 5/1989 | Brantigan | |
| 5,263,937 A * | 11/1993 | Shipp | A61B 17/3417 606/167 |

(Continued)

FOREIGN PATENT DOCUMENTS

| | | |
|---|---|---|
| CN | 102026584 | 4/2011 |
| CN | 102026584 A | 4/2011 |

(Continued)

OTHER PUBLICATIONS

First Office Action of May 3, 2017 for the State Intellectual Property Office of China (SIPA) for the counterpart application with the Serial No. 201480027310.0—EN translation.

(Continued)

*Primary Examiner* — Lynnsy M Summitt
(74) *Attorney, Agent, or Firm* — NIXON & VANDERHYE

(57) ABSTRACT

An orthopedic implant kit comprising a lockable poly-axial screw, a tissue dilatation sleeve, a screw driver, a screw extender, a rod, rod-reduction device, a set screw driver, a torque limiting device and a screw releasing device.

9 Claims, 24 Drawing Sheets

(56) References Cited

U.S. PATENT DOCUMENTS

| | | | |
|---|---|---|---|
| 5,304,119 A * | 4/1994 | Balaban | A61M 31/00 |
| | | | 604/511 |
| 5,354,302 A * | 10/1994 | Ko | A61B 1/00087 |
| | | | 604/161 |
| 5,669,909 A | 9/1997 | Zdeblick | |
| 5,728,098 A | 3/1998 | Sherman | |
| 5,752,970 A * | 5/1998 | Yoon | A61B 17/3498 |
| | | | 604/167.03 |
| 5,797,918 A | 8/1998 | McGuire | |
| 5,814,073 A * | 9/1998 | Bonutti | A61B 17/3439 |
| | | | 606/232 |
| 5,904,685 A * | 5/1999 | Walawalkar | A61F 2/0805 |
| | | | 606/104 |
| 5,913,860 A | 6/1999 | Scholl | |
| 6,113,601 A | 9/2000 | Tatar | |
| 6,368,321 B1 | 4/2002 | Jackson | |
| 6,371,968 B1 | 4/2002 | Kogasaka et al. | |
| 6,423,064 B1 | 7/2002 | Kluger | |
| 6,551,316 B1 | 4/2003 | Rinner | |
| 6,644,087 B1 | 11/2003 | Ralph | |
| 6,716,214 B1 | 4/2004 | Jackson | |
| 6,726,699 B1 * | 4/2004 | Wright | A61B 17/3421 |
| | | | 606/185 |
| 6,743,231 B1 | 6/2004 | Gray | |
| 6,849,064 B2 * | 2/2005 | Hamada | A61B 17/3439 |
| | | | 604/164.01 |
| 6,929,606 B2 * | 8/2005 | Ritland | A61B 17/1757 |
| | | | 600/210 |
| 6,939,318 B2 * | 9/2005 | Stenzel | A61B 17/3468 |
| | | | 604/60 |
| 7,056,329 B2 * | 6/2006 | Kerr | A61B 17/3496 |
| | | | 606/190 |
| 7,066,937 B2 | 6/2006 | Shluzas | |
| 7,079,883 B2 * | 7/2006 | Marino | A61B 17/3423 |
| | | | 128/898 |
| 7,144,393 B2 * | 12/2006 | DiPoto | A61B 17/3439 |
| | | | 606/1 |
| 7,160,300 B2 | 1/2007 | Jackson | |
| 7,179,225 B2 | 2/2007 | Shluzas et al. | |
| 7,204,851 B2 * | 4/2007 | Trieu | A61F 2/4611 |
| | | | 623/17.11 |
| 7,250,052 B2 * | 7/2007 | Landry | A61B 17/7085 |
| | | | 606/86 A |
| 7,374,534 B2 * | 5/2008 | Dalton | A61B 17/3439 |
| | | | 600/222 |
| 7,473,256 B2 * | 1/2009 | Assell | A61B 17/1757 |
| | | | 606/90 |
| 7,491,168 B2 | 2/2009 | Raymond et al. | |
| 7,520,879 B2 | 4/2009 | Justis | |
| 7,527,638 B2 | 5/2009 | Anderson | |
| 7,588,575 B2 | 9/2009 | Colleran | |
| 7,588,588 B2 * | 9/2009 | Spitler | A61B 17/7082 |
| | | | 606/279 |
| 7,604,655 B2 | 10/2009 | Warnick | |
| 7,651,502 B2 | 1/2010 | Jackson | |
| 7,666,189 B2 | 2/2010 | Gerber et al. | |
| 7,691,129 B2 | 4/2010 | Felix | |
| 7,691,132 B2 | 4/2010 | Landry | |
| 7,708,744 B2 * | 5/2010 | Soma | A61M 25/09041 |
| | | | 606/108 |
| 7,744,629 B2 | 6/2010 | Hestad et al. | |
| 7,749,232 B2 | 7/2010 | Salerni | |
| 7,749,233 B2 * | 7/2010 | Farr | A61B 17/7085 |
| | | | 606/86 A |
| 7,758,617 B2 * | 7/2010 | Lott | A61B 17/7086 |
| | | | 606/255 |
| 7,766,920 B2 * | 8/2010 | Ciccone | A61B 17/862 |
| | | | 606/86 R |
| 7,811,288 B2 | 10/2010 | Jones | |
| 7,842,044 B2 | 11/2010 | Runco et al. | |
| 7,846,093 B2 * | 12/2010 | Gorek | A61B 17/7002 |
| | | | 600/206 |
| 7,862,587 B2 | 1/2011 | Jackson | |
| 7,874,981 B2 * | 1/2011 | Whitman | A61B 17/3468 |
| | | | 600/184 |
| 7,892,238 B2 * | 2/2011 | DiPoto | A61B 17/7002 |
| | | | 606/103 |
| 7,892,259 B2 | 2/2011 | Biedermann et al. | |
| 7,922,725 B2 | 4/2011 | Darst Rice et al. | |
| 7,931,673 B2 | 4/2011 | Hestad et al. | |
| 7,951,172 B2 | 5/2011 | Chao | |
| 7,967,821 B2 | 6/2011 | Sicvol et al. | |
| 8,016,832 B2 | 9/2011 | Vonwiller et al. | |
| 8,016,862 B2 | 9/2011 | Felix et al. | |
| 8,034,086 B2 | 10/2011 | Iott | |
| 8,043,343 B2 * | 10/2011 | Miller | A61B 17/7038 |
| | | | 606/279 |
| 8,052,724 B2 | 11/2011 | Jackson | |
| 8,088,163 B1 | 1/2012 | Kleiner | |
| 8,114,085 B2 | 2/2012 | Von Jako | |
| 8,128,667 B2 | 3/2012 | Jackson | |
| 8,137,356 B2 | 3/2012 | Hestad et al. | |
| 8,152,810 B2 | 4/2012 | Jackson | |
| 8,167,911 B2 | 5/2012 | Shluzas et al. | |
| 8,197,519 B2 | 6/2012 | Schlaepfer | |
| 8,246,538 B2 * | 8/2012 | Gorek | A61B 17/0293 |
| | | | 600/206 |
| 8,246,665 B2 | 8/2012 | Butler et al. | |
| 8,262,662 B2 | 9/2012 | Beardsley | |
| 8,262,704 B2 | 9/2012 | Matthis et al. | |
| 8,282,604 B2 * | 10/2012 | Gresham | A61B 17/3421 |
| | | | 604/167.06 |
| 8,317,796 B2 | 11/2012 | Stihl et al. | |
| 8,366,747 B2 | 2/2013 | Shluzas | |
| 8,372,121 B2 | 2/2013 | Capote | |
| 8,372,131 B2 * | 2/2013 | Hestad | A61F 2/966 |
| | | | 623/1.2 |
| 8,382,805 B2 | 2/2013 | Wang et al. | |
| 8,394,109 B2 | 3/2013 | Hutton et al. | |
| 8,409,083 B2 * | 4/2013 | Mangiardi | A61B 17/3421 |
| | | | 600/184 |
| 8,465,546 B2 | 6/2013 | Jodaitis | |
| 8,469,960 B2 | 6/2013 | Hutton | |
| 8,562,652 B2 | 10/2013 | Biedermann | |
| 8,602,984 B2 * | 12/2013 | Raymond | A61B 17/02 |
| | | | 600/219 |
| 8,603,094 B2 | 12/2013 | Walker et al. | |
| 8,603,145 B2 | 12/2013 | Forton | |
| 8,608,746 B2 | 12/2013 | Kolb et al. | |
| 8,617,218 B2 | 12/2013 | Justis et al. | |
| 8,636,783 B2 | 1/2014 | Crall et al. | |
| 8,734,515 B2 * | 5/2014 | Frey | A61B 17/025 |
| | | | 606/90 |
| 8,747,407 B2 * | 6/2014 | Gorek | A61B 17/0206 |
| | | | 606/267 |
| 8,834,527 B2 * | 9/2014 | Hutton | A61B 17/7037 |
| | | | 606/279 |
| 8,858,621 B2 * | 10/2014 | Oba | A61B 17/3468 |
| | | | 623/2.11 |
| 8,870,878 B2 | 10/2014 | Gorek | |
| 8,876,710 B2 * | 11/2014 | Ferreira | A61B 17/3439 |
| | | | 600/206 |
| 9,050,139 B2 | 6/2015 | Jackson | |
| 9,066,758 B2 | 6/2015 | Justis et al. | |
| 9,066,761 B2 | 6/2015 | McBride et al. | |
| 9,078,769 B2 * | 7/2015 | Farin | A61F 2/4465 |
| 9,101,401 B2 | 8/2015 | Dalton et al. | |
| 9,138,261 B2 | 9/2015 | Di Lauro et al. | |
| 9,204,909 B2 | 12/2015 | Rezach et al. | |
| 9,211,143 B2 | 12/2015 | Barry | |
| 9,211,149 B2 | 12/2015 | Hoefer et al. | |
| 9,326,798 B2 | 5/2016 | Kolb et al. | |
| 9,408,649 B2 | 8/2016 | Felix et al. | |
| 9,492,209 B2 | 11/2016 | Biedermann et al. | |
| 9,526,537 B2 | 12/2016 | Meyer et al. | |
| 9,554,789 B2 * | 1/2017 | Overes | A61B 90/57 |
| 9,585,702 B2 | 3/2017 | Hutton | |
| 9,655,653 B2 | 5/2017 | Lindner et al. | |
| 9,668,754 B2 * | 6/2017 | Pfeiffer | A61B 17/1604 |
| 9,707,019 B2 | 7/2017 | Miller et al. | |
| 9,795,771 B2 * | 10/2017 | Trieu | A61M 29/02 |

(56) References Cited

U.S. PATENT DOCUMENTS

| | | | |
|---|---|---|---|
| 9,814,488 B2* | 11/2017 | Tatsumi | A61B 17/3421 |
| 9,924,982 B2 | 3/2018 | Jackson | |
| 9,962,197 B2 | 5/2018 | Dandaniopoulos et al. | |
| 9,968,378 B1 | 5/2018 | Johnson | |
| 10,194,967 B2* | 2/2019 | Baynham | A61B 17/7004 |
| 10,258,228 B2* | 4/2019 | Genovese | A61B 1/32 |
| 10,398,543 B1* | 9/2019 | Solar | A61F 2/12 |
| 10,925,592 B2* | 2/2021 | Sandhu | A61B 17/3468 |
| 11,154,286 B2* | 10/2021 | Seifert | A61B 17/3462 |
| 11,272,835 B2* | 3/2022 | Hsu | A61B 1/00135 |
| 11,464,577 B2* | 10/2022 | Bush, Jr. | A61B 17/162 |
| 11,590,326 B2* | 2/2023 | Wheeler | A61M 25/0668 |
| 11,707,267 B2* | 7/2023 | Sweeney | A61B 50/30 600/201 |
| 11,744,447 B2* | 9/2023 | Thommen | A61B 1/00154 606/90 |
| 11,903,620 B2* | 2/2024 | Richter | A61B 17/7091 |
| 2002/0193822 A1* | 12/2002 | Hung | A61B 17/3439 606/198 |
| 2003/0114860 A1 | 6/2003 | Cavagna | |
| 2003/0191371 A1* | 10/2003 | Smith | A61B 17/02 600/210 |
| 2004/0144149 A1 | 7/2004 | Strippgen | |
| 2004/0243139 A1* | 12/2004 | Lewis | A61B 17/8891 606/301 |
| 2005/0131408 A1 | 6/2005 | Sicvol | |
| 2005/0192570 A1 | 9/2005 | Jackson | |
| 2005/0192579 A1 | 9/2005 | Jackson | |
| 2005/0240197 A1 | 10/2005 | Kmiec | |
| 2005/0245928 A1 | 11/2005 | Colleran | |
| 2006/0036244 A1 | 2/2006 | Spitler et al. | |
| 2006/0079903 A1* | 4/2006 | Wong | A61B 17/8891 606/328 |
| 2006/0089644 A1 | 4/2006 | Felix | |
| 2006/0106415 A1* | 5/2006 | Gabbay | A61B 17/3468 606/198 |
| 2006/0111712 A1 | 5/2006 | Jackson | |
| 2006/0111715 A1 | 5/2006 | Jackson | |
| 2006/0212062 A1* | 9/2006 | Farascioni | A61B 17/3439 606/191 |
| 2006/0217719 A1 | 9/2006 | Albert | |
| 2006/0235427 A1 | 10/2006 | Thomas | |
| 2006/0241599 A1 | 10/2006 | Konieczynski | |
| 2007/0078460 A1 | 4/2007 | Frigg | |
| 2007/0106123 A1 | 5/2007 | Gorek | |
| 2007/0198045 A1* | 8/2007 | Morton | A61M 29/00 606/191 |
| 2007/0233091 A1 | 10/2007 | Naifeh | |
| 2007/0239159 A1 | 10/2007 | Altarac | |
| 2007/0261868 A1 | 11/2007 | Gross | |
| 2007/0270866 A1 | 11/2007 | Von Jako | |
| 2007/0270875 A1* | 11/2007 | Bacher | A61B 17/025 606/90 |
| 2008/0012111 A1 | 1/2008 | Pu | |
| 2008/0039839 A1 | 2/2008 | Songer | |
| 2008/0114403 A1* | 5/2008 | Kuester | A61B 17/7037 606/264 |
| 2008/0119852 A1 | 5/2008 | Dalton | |
| 2008/0147129 A1 | 6/2008 | Biedermann | |
| 2008/0154279 A1 | 6/2008 | Schumacher | |
| 2008/0200918 A1 | 8/2008 | Spitler | |
| 2008/0243189 A1 | 10/2008 | Purcell | |
| 2008/0262318 A1 | 10/2008 | Gorek | |
| 2008/0294172 A1 | 11/2008 | Baumgart | |
| 2008/0294203 A1 | 11/2008 | Kovach | |
| 2009/0171391 A1 | 7/2009 | Hutton | |
| 2009/0204159 A1 | 8/2009 | Justis | |
| 2009/0221879 A1* | 9/2009 | Gorek | A61B 17/708 606/279 |
| 2009/0222044 A1* | 9/2009 | Gorek | A61B 17/0218 606/279 |
| 2009/0222045 A1 | 9/2009 | Gorek | |
| 2009/0281571 A1 | 11/2009 | Weaver | |
| 2009/0306586 A1* | 12/2009 | Ross | A61B 17/3439 604/93.01 |
| 2010/0049003 A1* | 2/2010 | Levy | A61B 17/3439 600/199 |
| 2010/0152785 A1 | 6/2010 | Forton et al. | |
| 2010/0292742 A1 | 11/2010 | Stad | |
| 2010/0312103 A1 | 12/2010 | Gorek | |
| 2011/0040328 A1 | 2/2011 | Miller et al. | |
| 2011/0106179 A1 | 5/2011 | Prevost | |
| 2011/0166606 A1 | 7/2011 | Stihl et al. | |
| 2011/0172718 A1 | 7/2011 | Felix et al. | |
| 2011/0184465 A1* | 7/2011 | Boehm | A61B 17/7037 606/264 |
| 2011/0245883 A1 | 10/2011 | Dall | |
| 2011/0263945 A1 | 10/2011 | Peterson et al. | |
| 2011/0313460 A1 | 12/2011 | McLean et al. | |
| 2011/0319896 A1 | 12/2011 | Papenfuss | |
| 2012/0022575 A1* | 1/2012 | Mire | A61B 17/0293 606/198 |
| 2012/0022597 A1* | 1/2012 | Gephart | A61B 17/7091 606/279 |
| 2012/0031792 A1 | 2/2012 | Petit | |
| 2012/0186411 A1 | 7/2012 | Lodahi | |
| 2013/0012955 A1* | 1/2013 | Lin | A61M 29/00 606/104 |
| 2013/0012999 A1 | 1/2013 | Petit | |
| 2013/0023941 A1 | 1/2013 | Jackson et al. | |
| 2013/0053896 A1* | 2/2013 | Voyadzis | A61B 17/1671 606/279 |
| 2013/0096624 A1 | 4/2013 | Di Lauro et al. | |
| 2014/0031828 A1 | 1/2014 | Patel | |
| 2014/0046385 A1 | 2/2014 | Asaad | |
| 2014/0052187 A1 | 2/2014 | McBride | |
| 2014/0100613 A1 | 4/2014 | Iott et al. | |
| 2014/0128878 A1 | 5/2014 | O'Neil | |
| 2014/0171955 A1 | 6/2014 | Smith | |
| 2014/0277203 A1 | 9/2014 | Atoulikian | |
| 2014/0288655 A1 | 9/2014 | Parry | |
| 2015/0066042 A1 | 3/2015 | Cummins et al. | |
| 2015/0265322 A1 | 9/2015 | Jackson | |
| 2015/0351810 A1 | 12/2015 | Lindner et al. | |
| 2016/0089186 A1 | 3/2016 | Beyer | |
| 2016/0166304 A1 | 6/2016 | Stad | |
| 2016/0287294 A1 | 10/2016 | Kubo | |
| 2016/0346026 A1 | 12/2016 | Bootwala | |
| 2016/0374825 A1 | 12/2016 | Kleiner | |
| 2017/0095272 A1 | 4/2017 | Hutton et al. | |
| 2017/0143384 A1 | 5/2017 | Hutton et al. | |
| 2017/0181774 A1 | 6/2017 | Cahill | |
| 2017/0181775 A1 | 6/2017 | Jackson | |
| 2017/0189082 A1 | 7/2017 | Petit | |
| 2017/0265892 A1* | 9/2017 | Winegar | A61B 17/3415 |
| 2017/0348037 A1 | 12/2017 | Sexson | |
| 2018/0146990 A1* | 5/2018 | Manzanares | A61B 17/7092 |
| 2018/0214186 A1 | 8/2018 | Beyer | |
| 2018/0303631 A1 | 10/2018 | Phan | |
| 2021/0153968 A1* | 5/2021 | Peterson | A61B 17/7082 |
| 2022/0023513 A1* | 1/2022 | Wheeler | A61M 1/04 |

FOREIGN PATENT DOCUMENTS

| | | |
|---|---|---|
| CN | 202446242 | 9/2012 |
| CN | 202497225 U | 10/2012 |
| CN | 203777040 | 8/2014 |
| CN | 203777040 U | 8/2014 |
| CN | 105662662 A | 6/2016 |
| CN | 1005662662 | 6/2016 |
| EP | 1/26264 | 11/2006 |
| EP | 1726264 A1 | 11/2006 |
| EP | 1854587 A2 | 11/2007 |
| EP | 1994892 A1 | 11/2008 |
| EP | 1994902 | 11/2008 |
| EP | 1994902 A2 | 11/2008 |
| EP | 2198793 A2 | 6/2010 |
| EP | 2283787 | 2/2011 |
| EP | 2283787 A1 | 2/2011 |
| EP | 2522287 | 11/2012 |
| EP | 2522287 A1 | 11/2012 |

(56) References Cited

FOREIGN PATENT DOCUMENTS

| | | |
|---|---|---|
| EP | 2692304 A1 | 2/2014 |
| FR | 2712521 A1 | 5/1995 |
| JP | 2007283101 | 11/2007 |
| JP | 2011500267 | 1/2011 |
| JP | 2011500267 A | 1/2011 |
| JP | 2012507316 | 3/2012 |
| JP | 2013515580 | 5/2013 |
| TW | M273326 U | 8/2005 |
| WO | 9819616 A1 | 5/1998 |
| WO | WO 9819616 | 5/1998 |
| WO | 2005060837 A2 | 7/2005 |
| WO | WO 2005060837 | 7/2005 |
| WO | 2006045089 A2 | 4/2006 |
| WO | WO 2006045089 | 4/2006 |
| WO | 2006091863 A2 | 8/2006 |
| WO | WO 2006091863 | 8/2006 |
| WO | 2006130179 A2 | 12/2006 |
| WO | WO 2006130179 | 12/2006 |
| WO | 2007092870 A2 | 8/2007 |
| WO | WO2007092870 | 8/2007 |
| WO | 2007117366 A2 | 10/2007 |
| WO | WO2007117366 | 10/2007 |
| WO | 2008097974 A2 | 8/2008 |
| WO | WO 2008097974 | 8/2008 |
| WO | 2009055026 A1 | 4/2009 |
| WO | 2009055034 A1 | 4/2009 |
| WO | WO 2009055026 | 4/2009 |
| WO | WO 2009055034 | 4/2009 |
| WO | 2009114422 A2 | 9/2009 |
| WO | WO 2009114422 | 9/2009 |
| WO | 2009137246 A1 | 11/2009 |
| WO | WO 2009137246 | 11/2009 |
| WO | WO 2010052462 | 5/2010 |
| WO | WO 2011080426 | 7/2011 |

OTHER PUBLICATIONS

Indian first Office Action dated Sep. 10, 2020 for Application IN 10594/DELNP/2015.
International Search Report mailed Nov. 25, 2014 in International Application No. PCTIIB2014/060979, 5 pages.
Japanese Appeal Decision dated Aug. 18, 2020 for Application No. 2016-513463—translation EN.
Japanese Office Action issued by the Japanese Patent Office in the counterpart Japanese Application No. 2016-513463 Feb. 6, 2018, 9 pages + English translation.
Japanese Office Action issued by the Japanese Patent Office in the counterpart Japanese Application No. 2016-513463 of Aug. 14, 2018 and English translation thereof.
Notification of granting patent right of Jun. 6, 2019 for the State Intellectual Property Office of China (SIPA) for the counterpart application with the Serial No. 201480027310.0.
Office Action of Aug. 20, 2019 from the Japanese Patent Office ("JPO") for counterpart application with Application Serial No. JP2018-199618 with English Translation.
Opposition against European Patent No. 2 526 888 (EPO Application No. 12 177 688.4) of Apr. 21, 2018, EP counterpart of U.S. Pat. Pub. No. 2017/0189082.
Opposition against European Patent No. 2 526 888, Oppnent Response of Mar. 31, 2020.
Second Office Action issued from the European Patent Office (EPO) as an Article 94(3) EPC Communication of Aug. 29, 2018 in the counterpart application with the Serial No. 14 734 227.3.
Second Office Action of Feb. 5, 2018 for the State Intellectual Property Office of China (SIPA) for the counterpart application with the Serial No. 201480027310.0.
Third Office Action issued from the European Patent Office (EPO) as an Article 94(3) EPC Communication of May 3, 2019 for Serial No. 14 734 227.3.
Third Party Observation filed on Jun. 26, 2019 against EPO Patent Application No. EP20100810769 (Publication No. EP2519180, corresponding to U.S. Pat. Pub. No. 2017/0189082).
Written Opinion of the ISA, mailed Nov. 25, 2014 for International Application No. PCTIIB2014/060979.
International Search Report, mailed Aug. 21, 2020 for International Application No. PCT/IB2020/052857.
Written Opinion of the ISA, mailed Aug. 21, 2020 for International Application No. PCT/IB2020/052857.
Indian Office Action mailed on Feb. 21, 2022, for Divisionnal Application No. IN 202118009679.
European Search Opinion for Application EP20196814.6 dated Jan. 14, 2021.
European Search Opinion for Application EP20196821.1 dated Jan. 19, 2021.
European Search Report for Application EP20196814.6 dated Jan. 14, 2021.
European Search Report for Application EP20196821.1 dated Jan. 19, 2021.
Japanese Office Action for Application No. JP 2020-073757 dated May 11, 2021 (in JP with translation in EN).

* cited by examiner

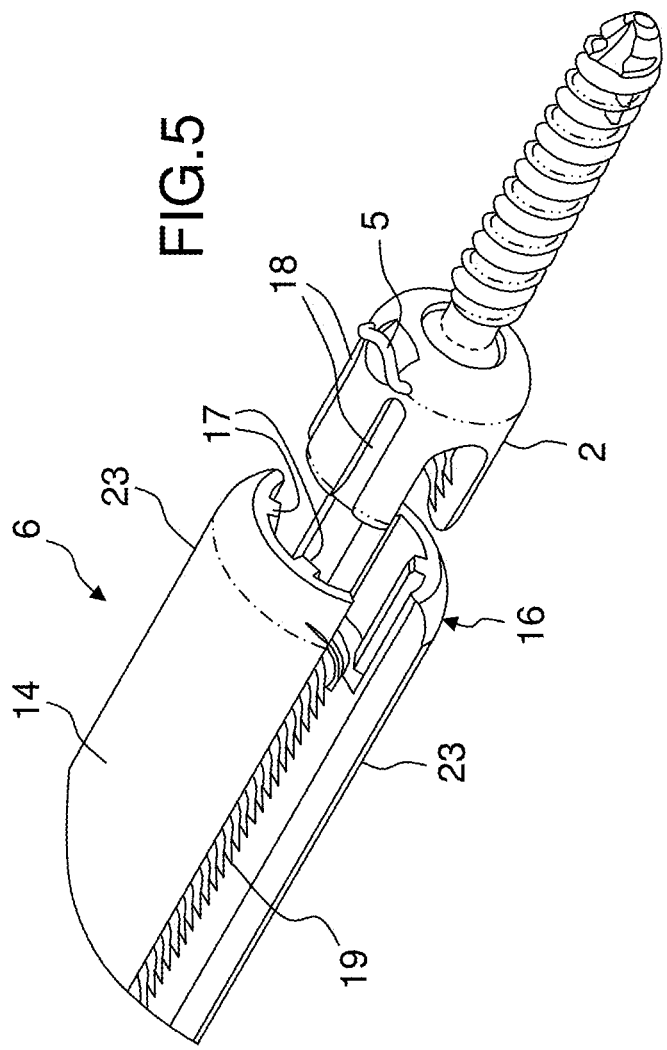
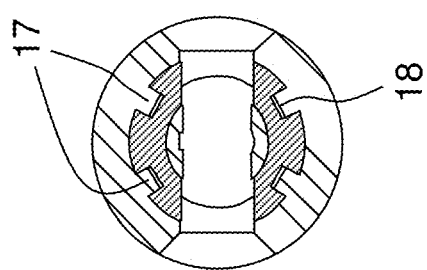
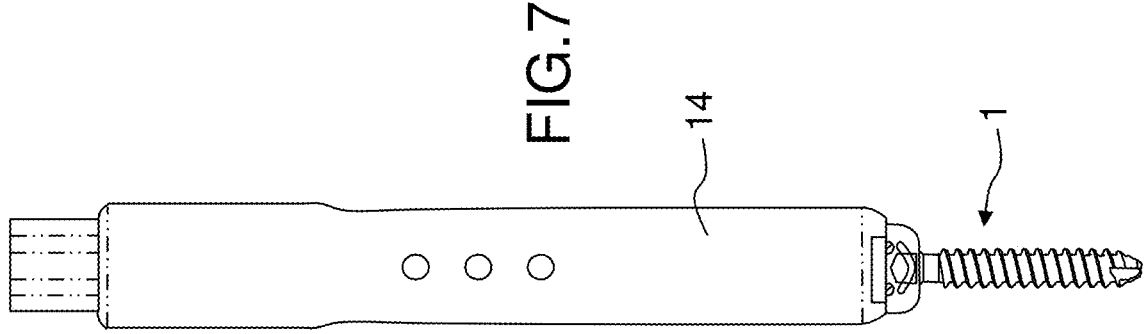

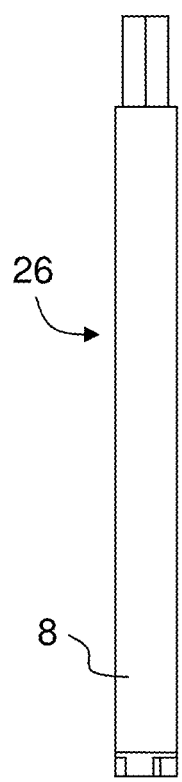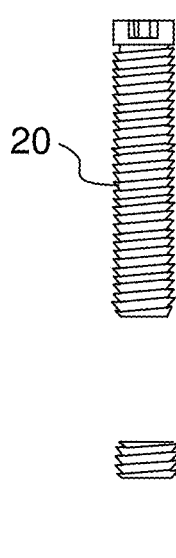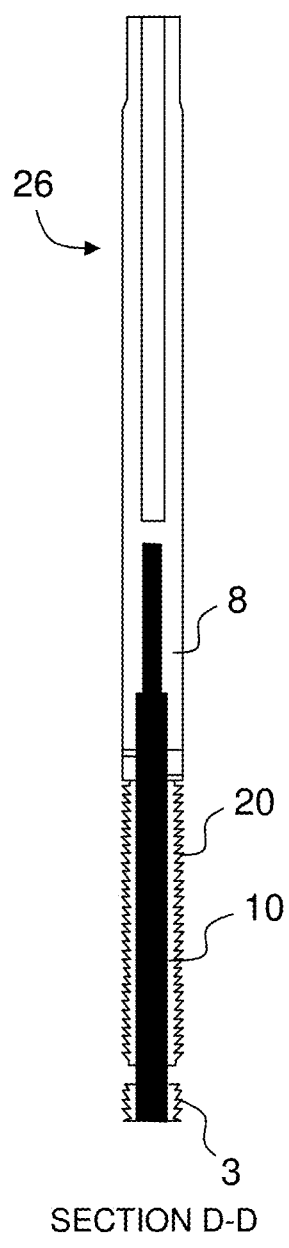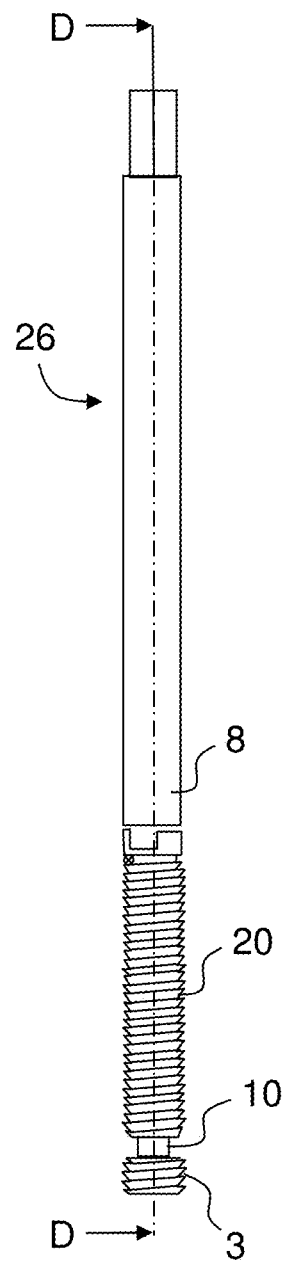
FIG.13A  FIG.13B  FIG.13C

ORTHOPEDIC IMPLANT KIT

CROSS-REFERENCE TO RELATED APPLICATIONS

The present application is a divisional application of U.S. Ser. No. 15/939,338, now U.S. Pat. No. 10,888,356, that was filed on Mar. 29, 2018, which is in turn a continuation application of U.S. Ser. No. 14/890,631, now U.S. Pat. No. 10,058,355, that was filed on Nov. 12, 2015, which is a United States national stage application of International patent application PCT/IB2014/060979, filed on Apr. 24, 2014, which designated the United States, and claims foreign priority to International patent application PCT/IB2013/053892, filed on May 13, 2013, the entire contents of all four (4) documents being herewith incorporated by reference.

FIELD OF INVENTION

The present invention relates to orthopedics and more precisely to orthopedic items such as pedicle screws, rods and spine cages. The invention also relates to instruments which are used for manipulating those items.

BACKGROUND

US 2013/0012999 discloses an orthopedic implant kit comprising several items, in particular a pedicle screw fixed to a mounting tube made of two half-shells which can be easily disassembled. Pedicle screws of the prior art can be divided in two main groups:
  Mono-axial screws: The direction of the screw main axis is fixed with respect the screw head;
  Poly-axial screws: The orientation of the screw main axis can be freely modified with respect to the screw head.
When implanting a pedicle screw into a bone several steps are needed. For almost each of those steps a dedicated instrument is used.

GENERAL DESCRIPTION OF THE INVENTION

An objective of the present invention is to reduce the number of items which are required for manipulating and fixing an orthopedic implant (pedicle screw, nut, rod, etc. . . . ).

Another objective is to reduce the number of instruments for manipulating those items.

Another objective is to facilitate the handling of the instruments.

Those objectives are met with the implant kit and the related items and instruments which are defined in the claims.

In a first embodiment the invention consists in an orthopedic implant kit comprising a lockable poly-axial screw, a tissue dilatation sleeve, a screw driver, a screw extender, a rod, rod-reduction means, a set screw driver, a torque limiting mechanism and a screw releasing instrument.

The lockable poly-axial orthopedic screw according to the invention comprises a head and a threaded portion which form two separate elements, fixed to each other but each element may be independently oriented along a specific direction. The threaded portion may, for instance, rotates around the screw head and may adopt several possible orientations. More precisely, the threaded portion may be oriented anywhere within a conical volume, the top of the cone corresponding to the contact point between the head and the threaded portion.

The screw furthermore comprises a locking element which, when activated, suppresses the relative movement between the threaded portion and the head. This configuration is named "mono-axial" because the threaded portion may be oriented along a single (fixed) axis with respect to the head. According one embodiment the locking element is a clip having a U-shape. In this case the head and the threaded portion contains cavities which are adapted to receive the branches of the U-shape clip.

Preferably, in the mono-axial mode the head may still freely rotate around its own axis, with respect to the threaded portion. Such a mechanism may be obtained with a U-shape clip and with an annular groove located around the upper part of the threaded portion. In this case the branches of the clip are sliding within the annular groove.

In another embodiment the screw head contains at least one longitudinal relief, such as a groove or a ridge, which is dimensioned in a way as to receive a corresponding relief, such as a ridge or a groove, which is located within the distal end of a screw extender.

In another embodiment the screw comprises a concave seat located in the proximal end of the threaded portion and a corresponding convex shape located at the distal part of the screw head. This configuration reduces the screw length and increases the strength and the rigidity of the system.

The screw extender according to the invention comprises a hollow cylindrical body made of two half tubes separated by two opposite longitudinal slots having an open end towards the cylindrical body distal part, this later one being dimensioned to receive and hold a screw head. The cylindrical body furthermore comprises an internal threaded part.

According to one embodiment the cylindrical body is made of a single piece and the distal part is radially expandable by its own elasticity, in such a way as to allow an easy clipping and subsequent releasing of a screw head.

To facilitate its radial expansion, the screw extender may include expanding means, for instance an internal rotatable tube which, when rotated pushes away the two half tubes from each other.

In a preferred embodiment the internal part of the cylindrical body distal end contains at least one relief, such as a ridge or a groove, which is dimensioned to be received within the longitudinal relief of a screw head which includes a corresponding relief, as mentioned previously. With this configuration it hinders the distal part of the half tubes to separate from each other by its own elasticity thus making a very strong attachment between the screw extender and the screw head. An additional benefit is that the relative rotation between the screw head and the cylindrical body is avoided.

In a preferred embodiment a rod reduction instrument is located within the cylindrical body. Advantageously the rod reduction instrument is essentially made of a shaft with a threaded distal part which is the counterpart of the cylindrical body internal threaded part. So when it is rotated within the cylindrical body the shaft may move along the cylindrical body main axis.

In another embodiment a set screw driver is (also or alternatively) located within said cylindrical body. In this case also, the set screw driver may also essentially be made of a shaft with a threaded distal part.

Advantageously the set screw driver comprises a torque limiting mechanism.

In one embodiment this mechanism includes a breakable pin and a thread free rotatable shaft. The pin is laterally crossing the rotatable shaft and its ends are fixed within the threaded rotatable shaft. The threaded and the threaded free shafts are rotatably linked to each other but when a certain torque is reached the pin breaks and each shaft may freely rotates with respect to the other shaft.

In another embodiment a screw releasing instrument is (also or alternatively) located within said cylindrical body.

Advantageously the screw releasing instrument is essentially made of a shaft with a threaded distal part.

In a particularly interesting embodiment, the same shaft with a threaded distal part is used for the rod reduction instrument (and potential sponylolisthesis), the set screw driver and the screw releasing mechanism.

The tissue dilatation sleeve according to the invention comprises a flexible conical part which is adapted to be temporarily fixed to the distal part of an instrument such as a screw extender as defined in the previous claims.

In one embodiment the conical part is made of several longitudinal flexible blades having each a substantially triangular shape.

DETAILED DESCRIPTION OF THE INVENTION

The invention will be better understood in the following part of this document, with non-limiting examples illustrated by the following figures:

FIG. 5 shows the distal part of a screw extender according to the invention, together with the screw of FIG. 2

FIG. 6 is a cross section of the screw extender distal part

FIG. 7 is a global view of a screw extender with a screw

Figure 12:
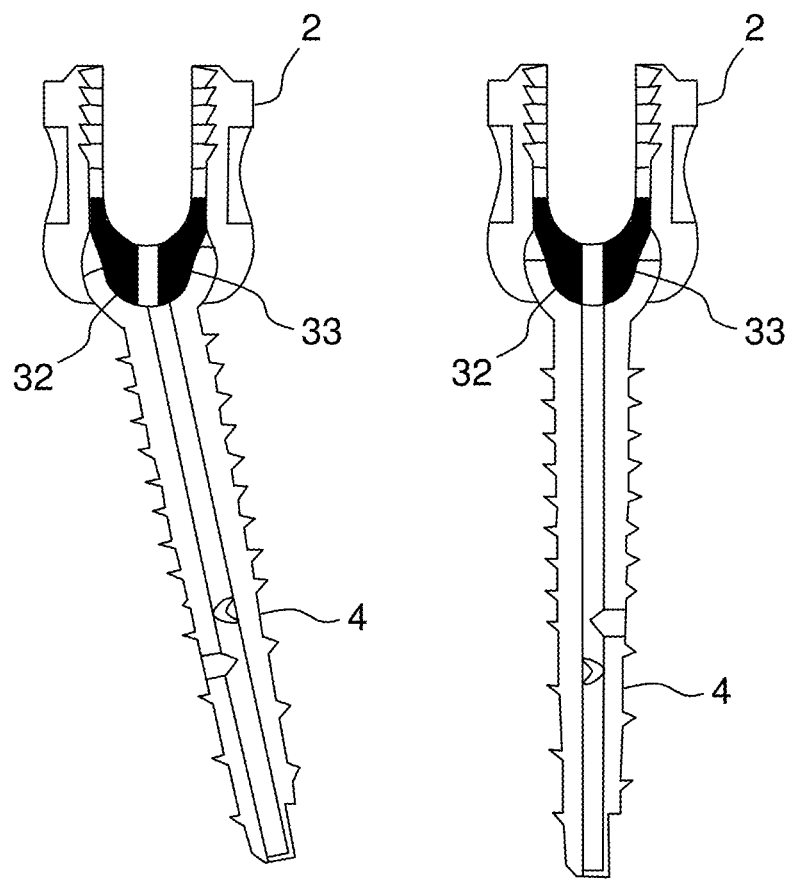
Figure 14:
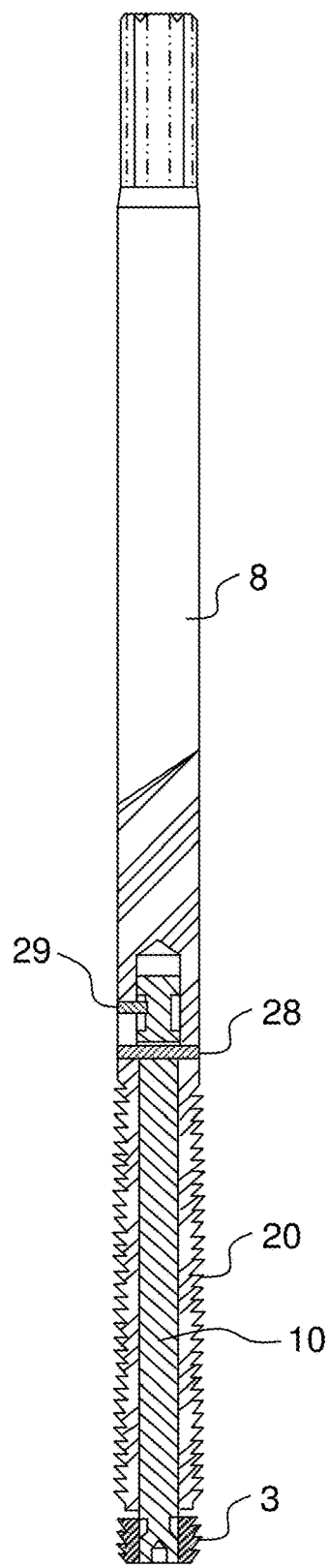
Figure 15:
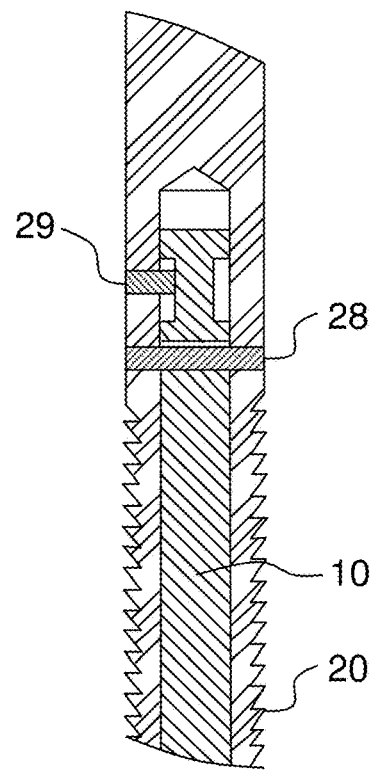
Figure 16:
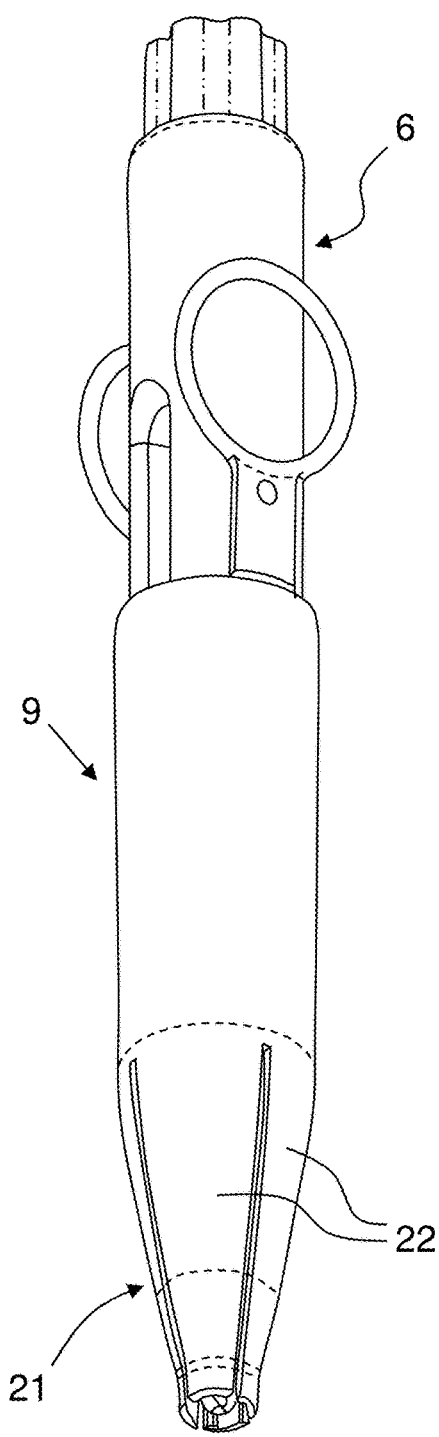
Figure 17:
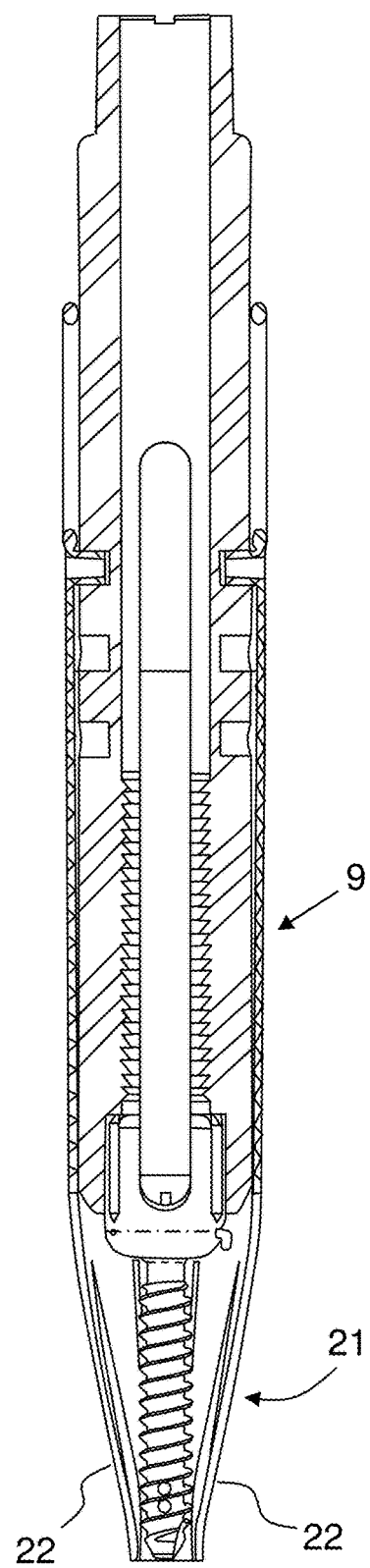
Figure 19:
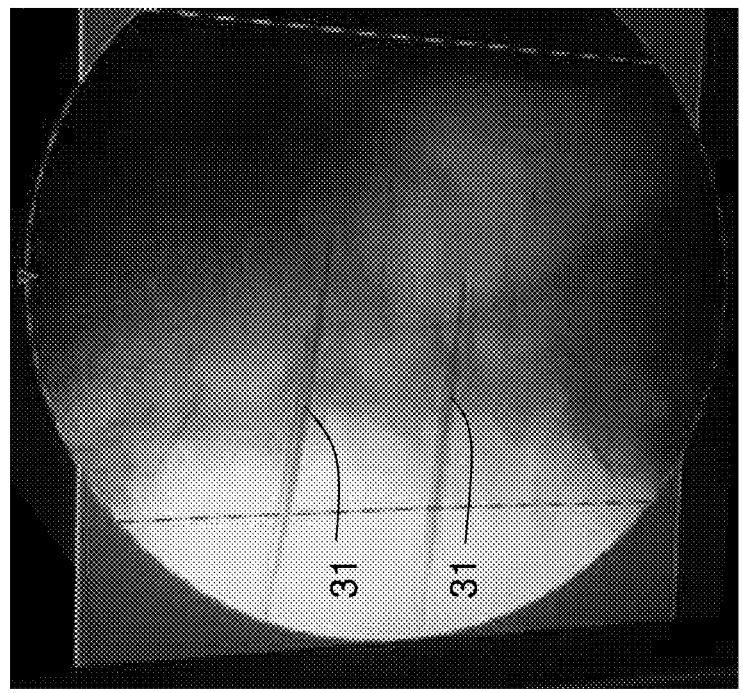
Figure 18:
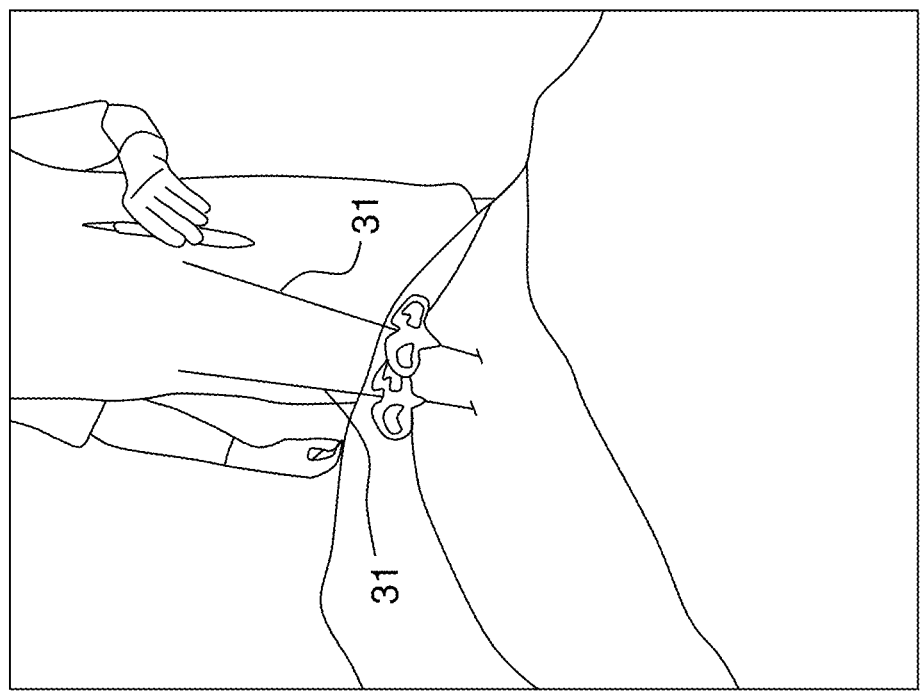
Figure 21:
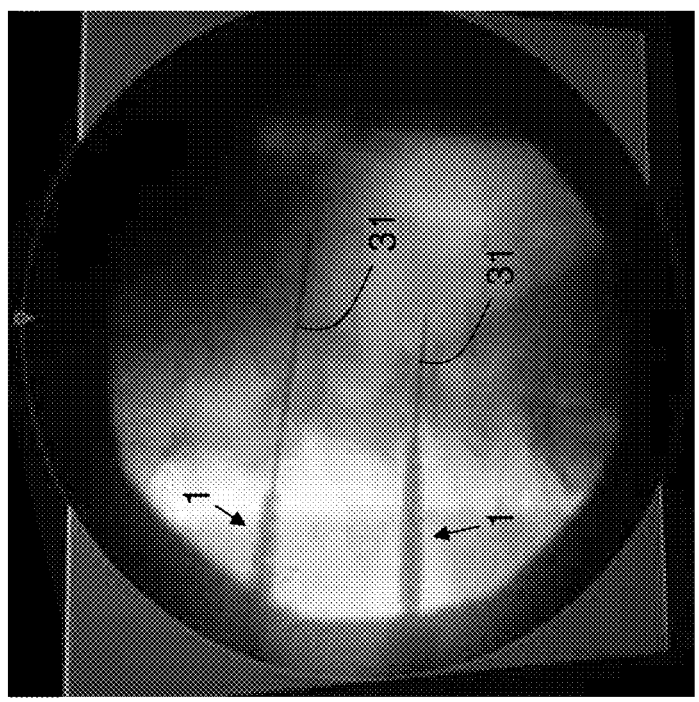
Figure 20:
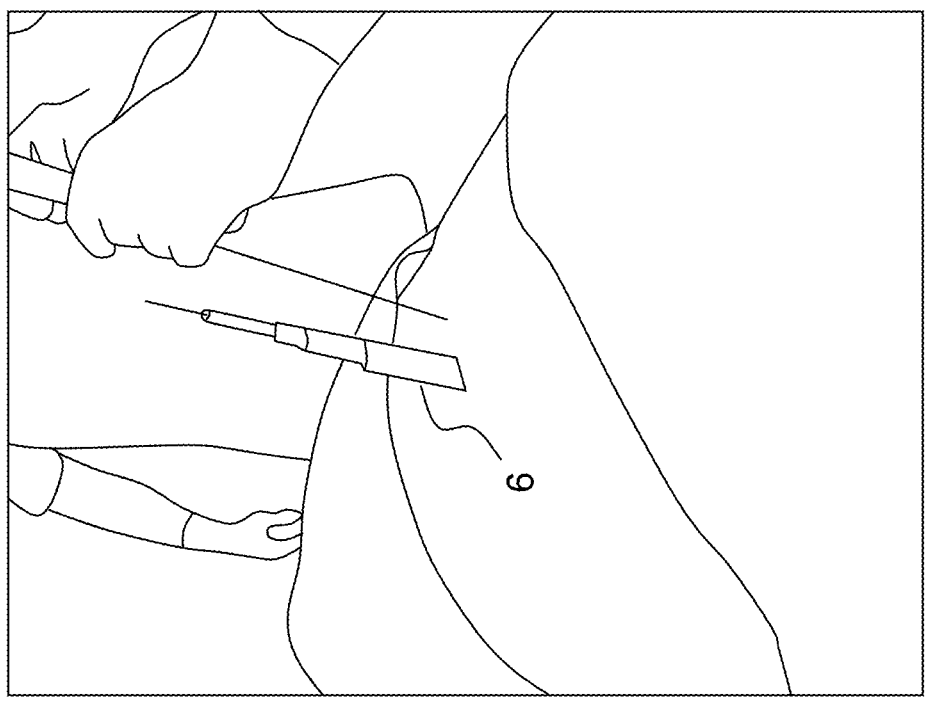

FIG. 12 shows another embodiment of a pedicle screw according to the invention FIGS. 13A to 13C show different views of a rotatable shaft which is used in a rod reduction instrument, a set screw driver and a screw releasing instrument FIGS. 14 and 15 illustrate a torque limiting mechanism FIGS. 16 and 17 show the use of a tissue dilatation sleeve FIGS. 18 to 38 show a procedure using an implant kit according to the invention

NUMERICAL REFERENCES USED IN THE FIGURES

1. Pedicle screw
2. Head
3. Set screw
4. Threaded portion
5. Locking element
6. Screw extender
7. Rod
8. Multi-use instrument upper part
9. Tissue dilatation sleeve
10. Torque driver
11. Head passage
12. Threaded portion passage
13. Branch
14. Cylindrical body
15. Slot
16. Cylindrical body distal part
17. Ridge
18. Groove
19. Screw extender internal threaded part
20. Multi-use instrument lower part
21. Conical part
22. Blade
23. Half tube
24. Screw driver
25. Handle
26. Multi-use instrument (Rod reduction/Set screw driver/screw release)
27. Rod inserting instrument
28. Breakable pin
29. Lateral pin
30. Circular groove
31. Puncturing needle/Guide wire
32. Concave screw top
33. Convex upper half ball The examples below more precisely relate to a thoracolumbar fusion system consisting of pedicle screws and rods combined with single use instruments. A typical pedicle screw system consists of the screw implants and the instruments for placing the screws.

Figure 1:
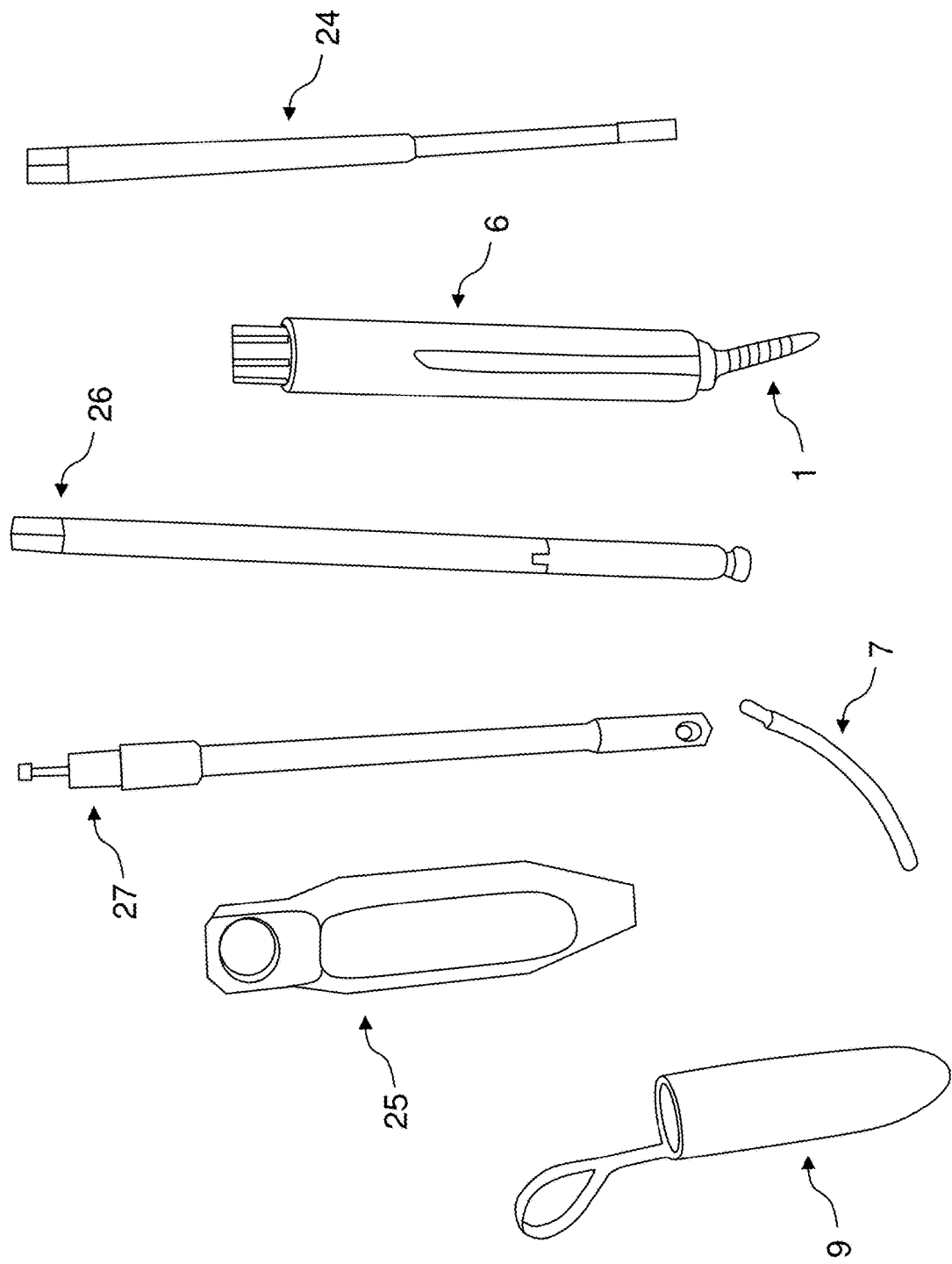
FIG. 1 shows an implant kit according to the invention

FIG. 1 shows an example of an implant kit according to the invention.

This kit contains a tissue dilatation sleeve 9, a handle 25, a rod 7, a rod inserting instrument 27, a shaft 26 which can be used as a rod reduction instrument and/or a set screw driver and/or a screw releasing instrument, a pedicle screw 1, a screw extender 6 and a screw driver 24.

Figure 2:
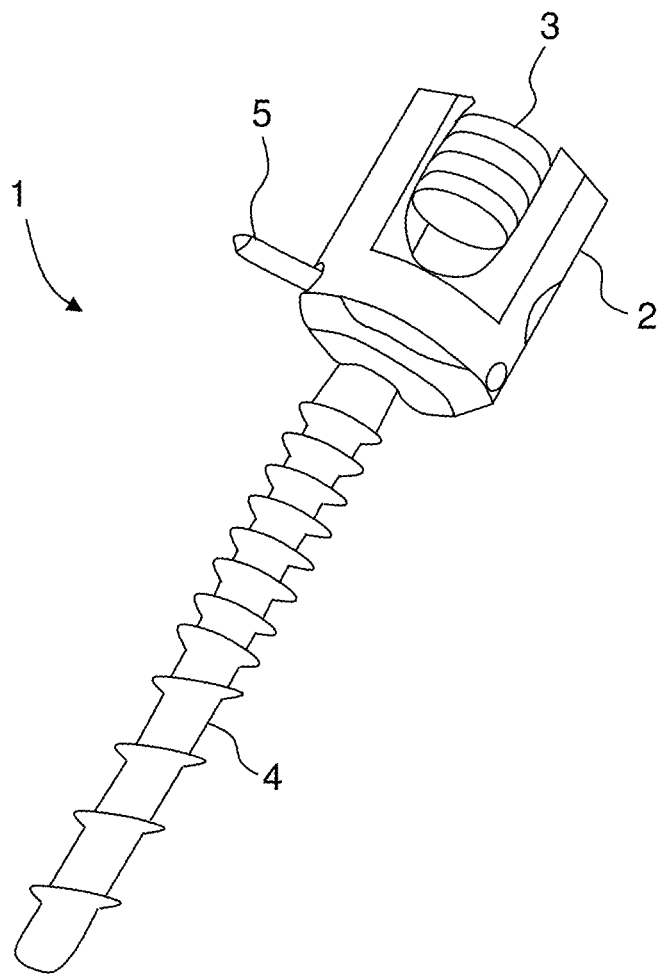
FIG. 2 shows an example of a lockable poly-axial pedicle screw according to the invention
Figure 3A:
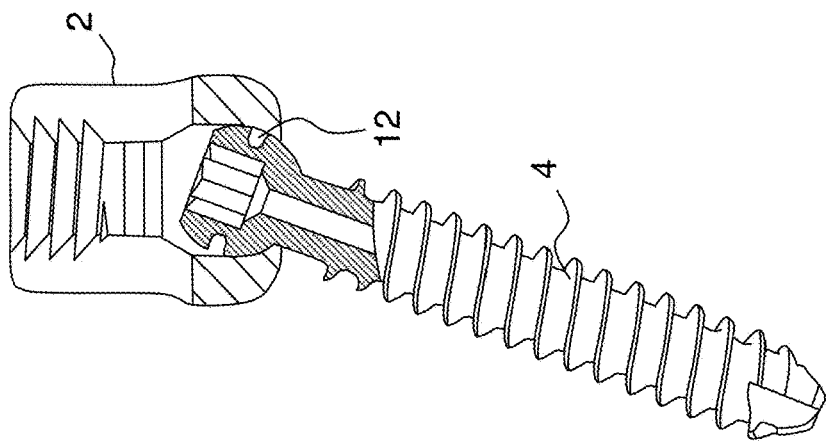
FIGS. 3A to 3C are cross-sections and partial cut views of the screw of FIG. 2
Figure 3B:
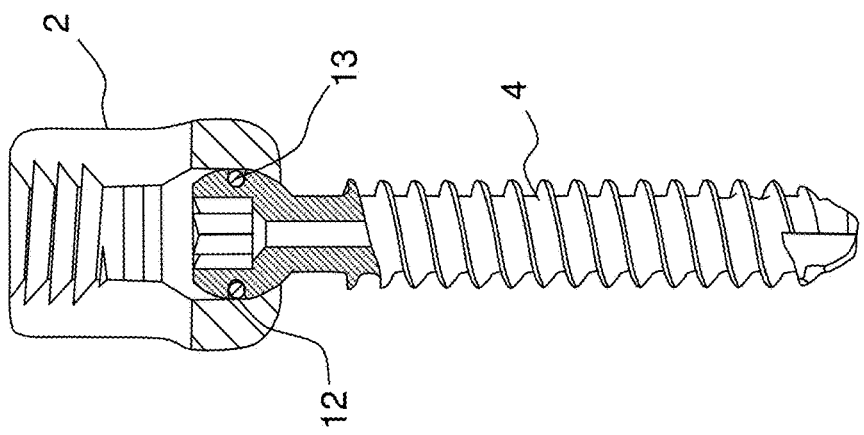
Figure 3C:
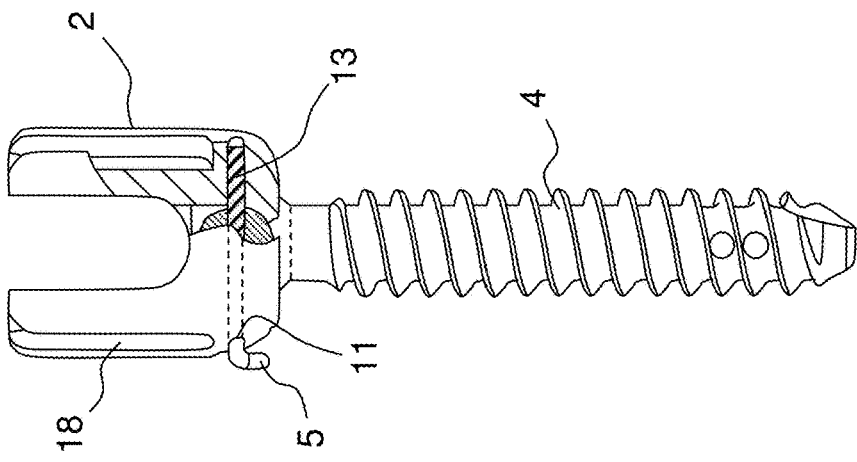
Figure 4:
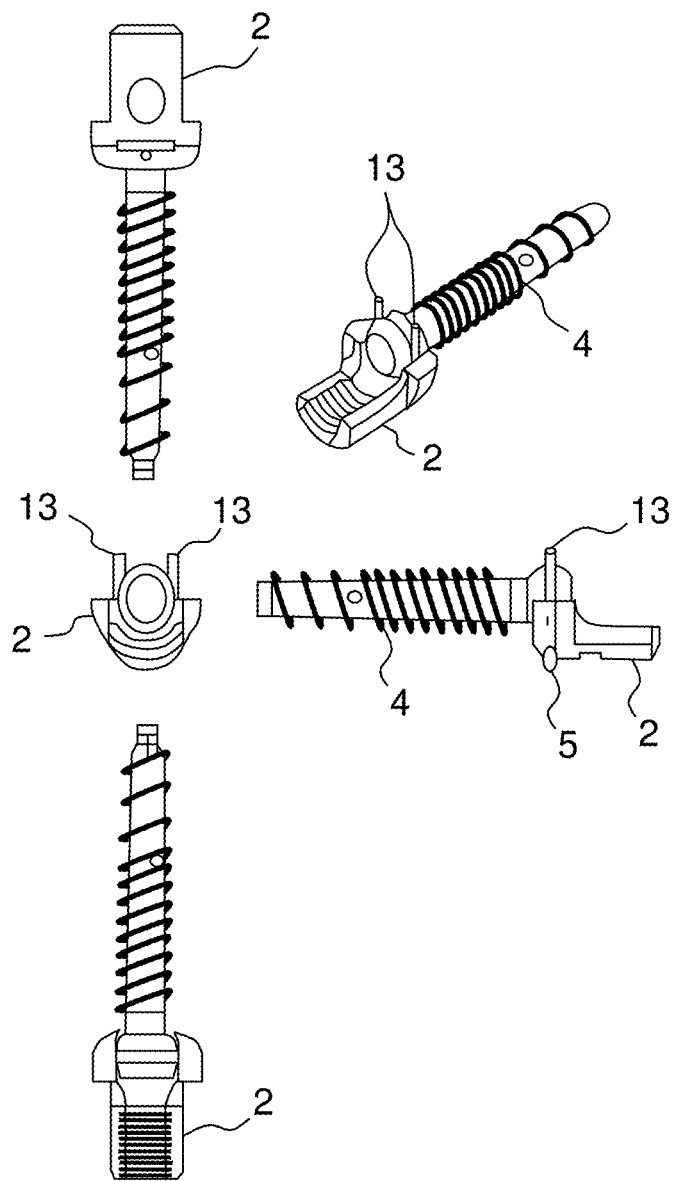
FIG. 4 represents different views (complete and partial) of the screw of FIG. 2

The lockable poly-axial screw 1 illustrated in particular in FIGS. 2 to 4 includes a head 2 and a threaded portion 4. FIG. 2 also shows a set screw 3 which may be fixed to the head after the insertion of a rod 7. The screw 1 furthermore comprises a locking element 5 having a U-shape. When the locking element 5 is fully inserted in the screw head 2 the orientation of threaded portion 4 is blocked with respect to the head 2. Inversely, when the locking element is retrieved, the threaded portion 4 can be freely oriented with respect to the screw head 2.

The lockable poly-axial screw according to the invention may therefore be transformed into a mono-axial screw, thus allowing having mono-axial and poly-axial capability in the same product. A blocking system defined previously allows the surgeon to choose if he/she wants to use the screw in mono-axial or poly-axial mode. As mentioned mono-axial capability is achieved by pushing the locking element (clip) 5 and poly-axial capability is achieved by removing the clip 5. The clip 5 is just an example of a blocking system; other technical solutions can also be imagined such as a pin.

Preferably, in the mono-axial mode the head may still freely rotate around its own axis, with respect to the threaded portion. Such a mechanism may be obtained with a U-shape clip and with an annular groove located around the upper part of the threaded portion. In this case the branches of the clip are sliding within the annular groove.

Any orientation of the axis can be considered when the mono-axial is used, i.e. the screw axis and the screw head may be oriented along different directions.

FIGS. 5 to 7 represent the attachment of a pedicle screw 1 to the distal end 16 of a screw extender 6, by inserting the screw head 2 within the distal end 16. In this operation the head 2 is guided with a plurality of ridges 17 located within the distal end 16 and grooves located on the head 2. With such a system the screw head is better retained within the screw extender 6.

Any suitable material can be used for the screw extender 6 (plastic, polymer, metal, etc. . . . ).

Figures 8A, 8B, 8C:
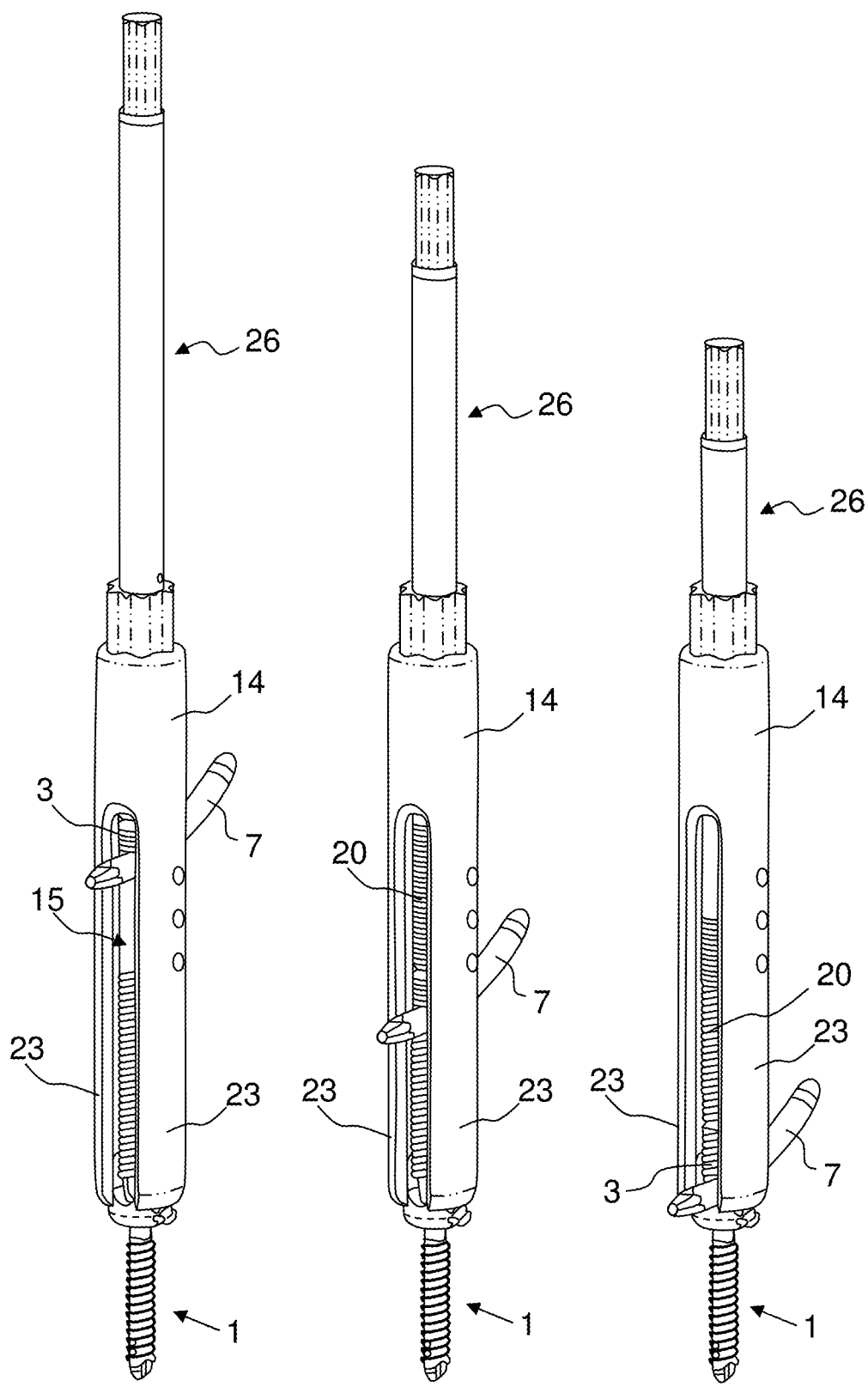
FIGS. 8A to 8C represent the positioning of the rod in the screw head, rod reduction and the tightening of the set screw

FIGS. 8A to 8C represent the positioning of the rod 7 in the screw head 2, a rod reduction and the tightening of the set screw 3 in the screw head 2.

The multi-use instrument 26 (see also FIGS. 13A to 13B) is defined by an upper part 8 and a lower (threaded) part 20.

The rod 7 may be pushed downwards by rotating the multi-use instrument 26 within the cylindrical body 14.

After the rod insertion within the head 2, the set screw 3 is fixed to the head 2 by further rotating the multi-use instrument 26.

Figure 9A:
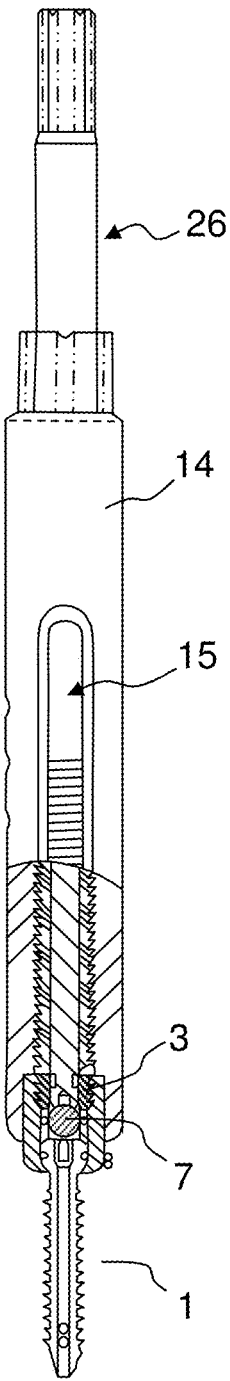
FIGS. 9A to 9C illustrate the release of the screw with respect to the screw extender
Figure 9B:
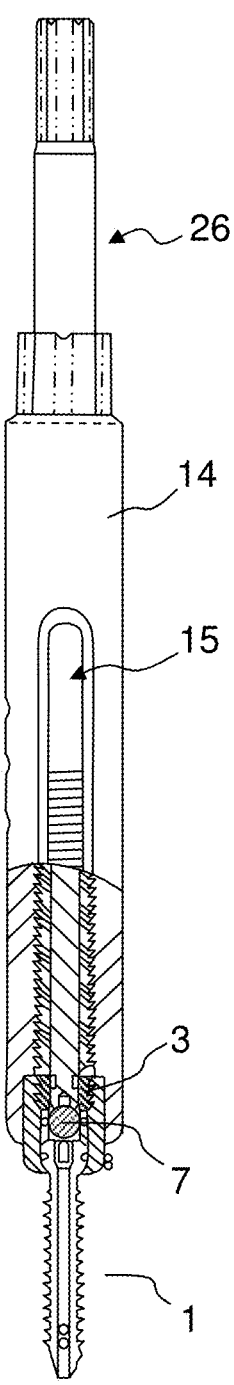
Figure 9C:
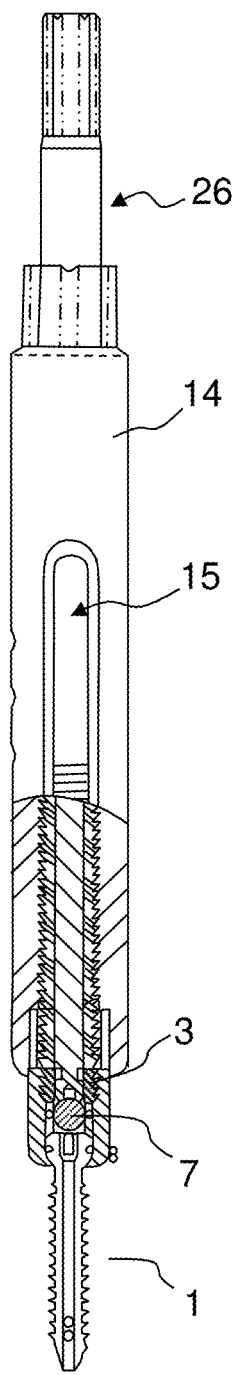

The multi-use instrument 26 is also provided with a torque limiting mechanism (see FIGS. 14 and 15). When the set screw 3 is fixed within the head 2 and the multi-use instrument 26 further rotated, the torque increases, up to a point where the pin 28 breaks. A further rotation of the multi-use instrument 26 has therefore no more effect on the set screw 3. From that point the further rotation of the multi-use instrument 26 only induces a downwards pressure on the screw head 2. The screw 1 is therefore progressively separated from the screw extender (see FIGS. 9A to 9C).

This screw releasing mechanism from an instrument offers the possibility to release the screw 1 from the screw extender without laterally expanding the screw extender 6.

It should be mentioned at this stage that this mechanism is not limited to the release of pedicle screws. Any other item may be used.

To summarize, the same instrument 26 can be used for rod reduction, for fixing a set screw to a screw head and for releasing a screw from a screw extender.

It should be underlined that the invention is not limited to this triple use of the same instrument. A double use is also comprised, for instance rod-reduction and fixation of the screw set to the screw head.

Figure 10:
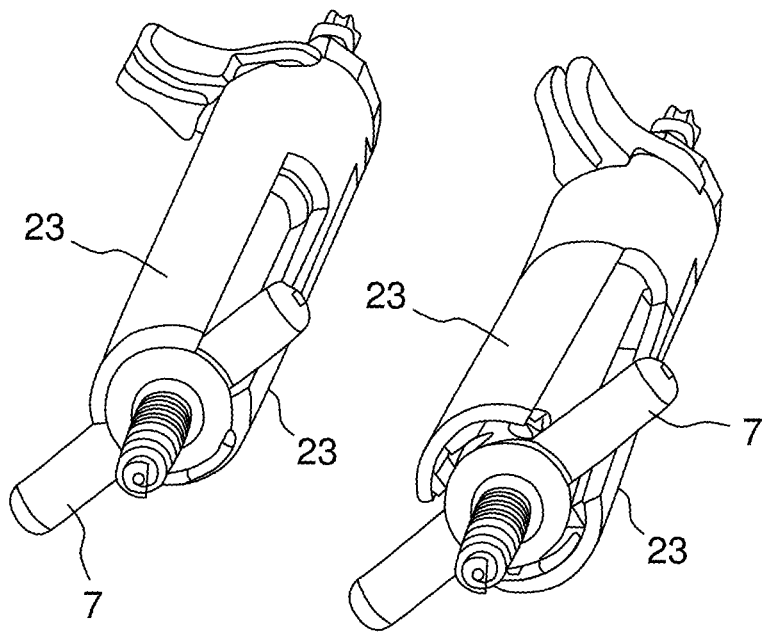
FIG. 10 shows a screw extender which includes a mechanism for laterally expanding the screw extender distal part
Figure 11:
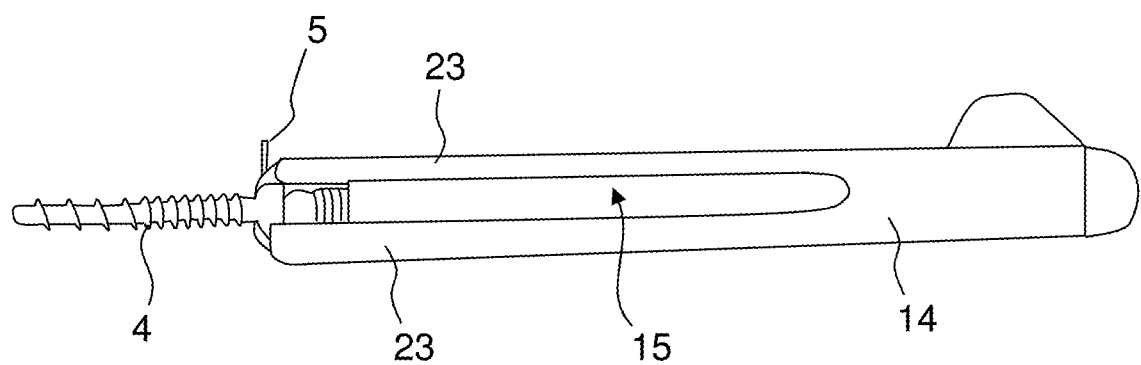
FIG. 11 is another representation of the screw extender of FIG. 10

FIGS. 10 and 11 show an alternative solution to attach a pedicle screw to an screw extender, by rotating an inside tube (not illustrated) the half-tubes 23 are expanded by their own elasticity. This allows a screw to be inserted and fixed to it by for example clamping the outer surface around the screw. The same principle can be used as an alternative to detach the screw extender from a screw.

The clamping system also achieves part of its rigidity, by resting on support surfaces on the screw head.

FIG. 12 shows a concave screw top 32, inside a convex upper half ball 33, allowing the rod 7 and the set screw 3 to be set lower in the screw head 2, thus decreasing the total build height, and increasing the strength and rigidity of the system.

FIGS. 16 and 17 represents a tissue dilatation sleeve 9 containing four triangular flexible blades 22 intervened into each other and forming a cone 21. The cone 21 is mounted at the tip of a screw extender 6, with a tear off spiral. This allows the tissue to be pushed aside as the screw extender 6 is inserted into a body. Once in place, the surgeon may remove the sleeve 9 while the screw extender remains in the body. Any suitable number of blades can be used for forming the cone.

FIGS. 18 to 38 show a procedure using the items which have been previously presented.

In a first step (FIGS. 18 and 19) two puncturing guide wires 31 are positioned in the spine.

A first screw extender 6 with a screw 1 attached and surrounded by a dilatation sleeve is then inserted through the tissue (FIGS. 20 and 21), and along the guide wire 31. The screw extender 6 is rotated and/or pushed.

Figure 23:
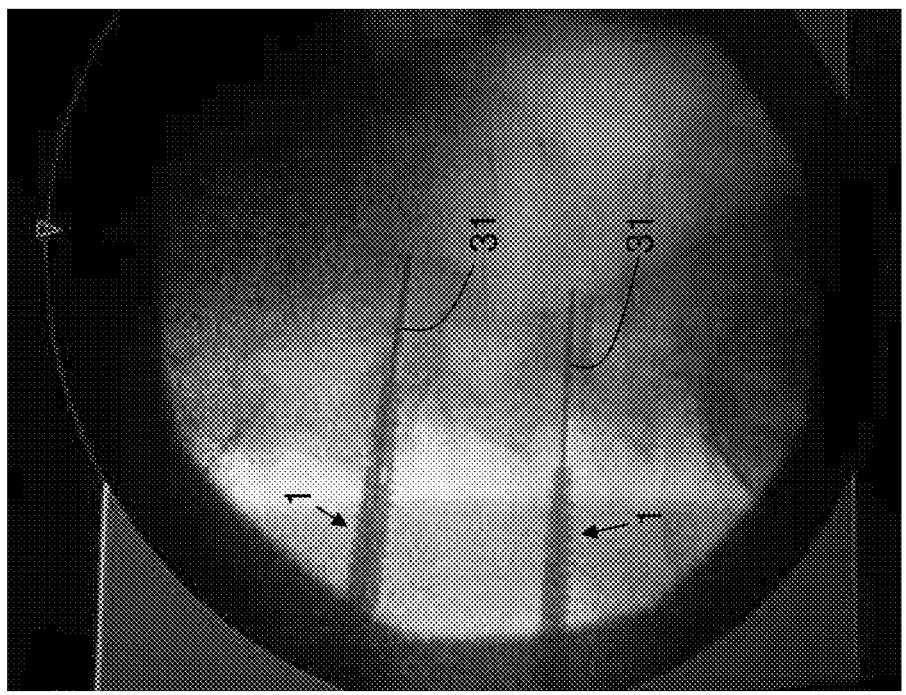
Figure 22:
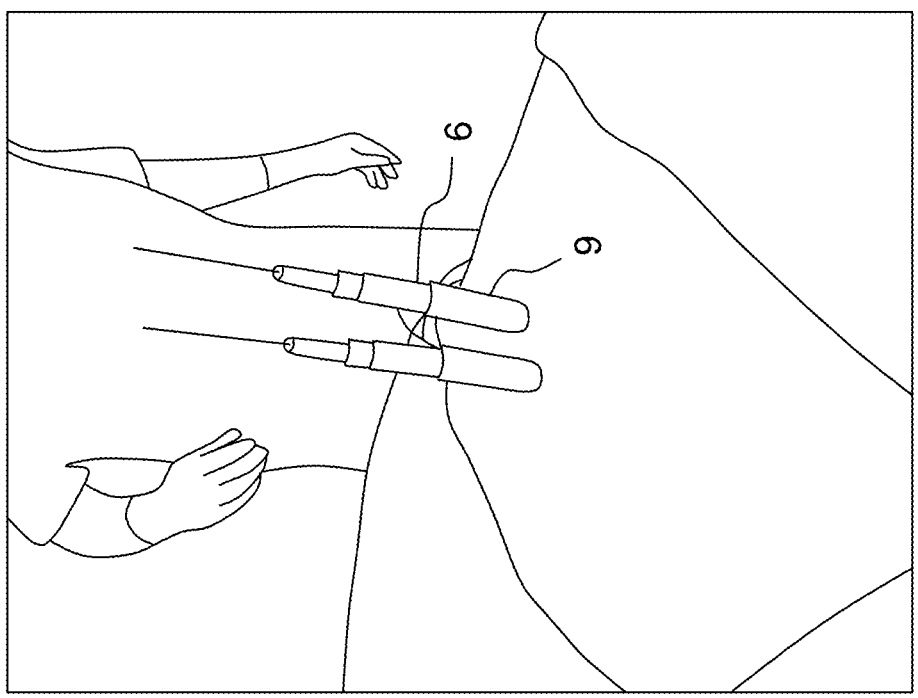

A similar operation is carried out with a second screw extender 6 and screw 1 (FIGS. 22 and 23).

Figure 25:
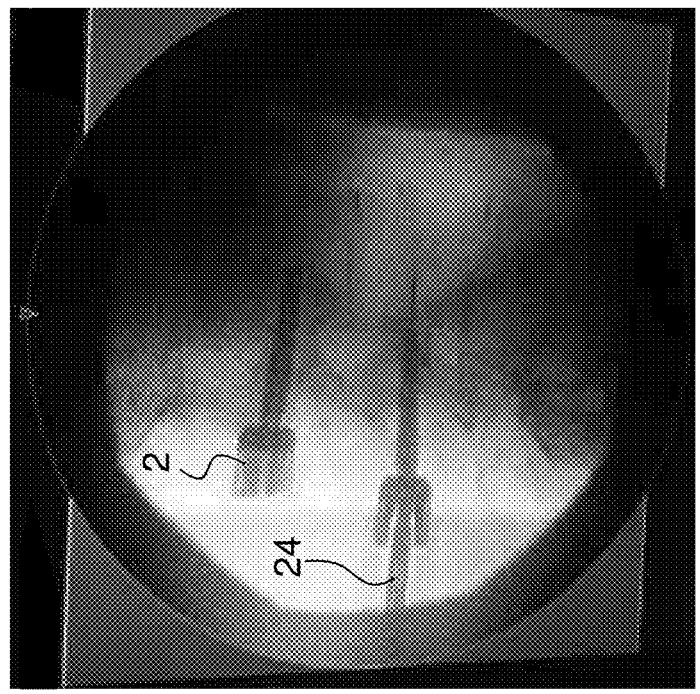
Figure 24:
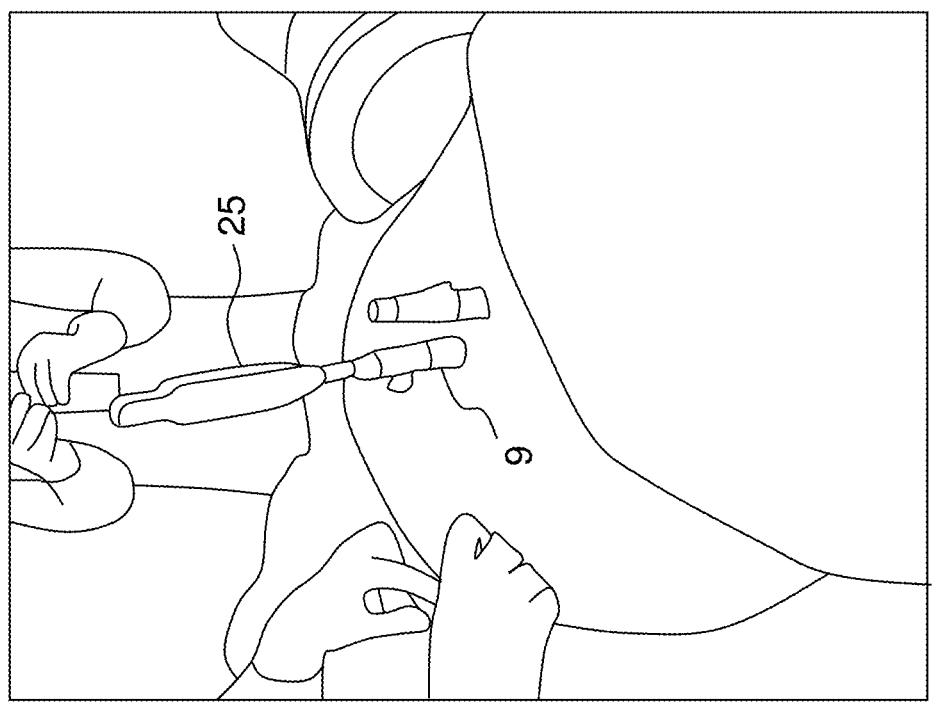

A screw driver 24 is inserted within the screw extender 6. Its distal end is introduced within the upper part of the screw threaded portion 4. The screws 1 are then rotated and enter the vertebrae (FIGS. 24 and 25).

Figure 27:
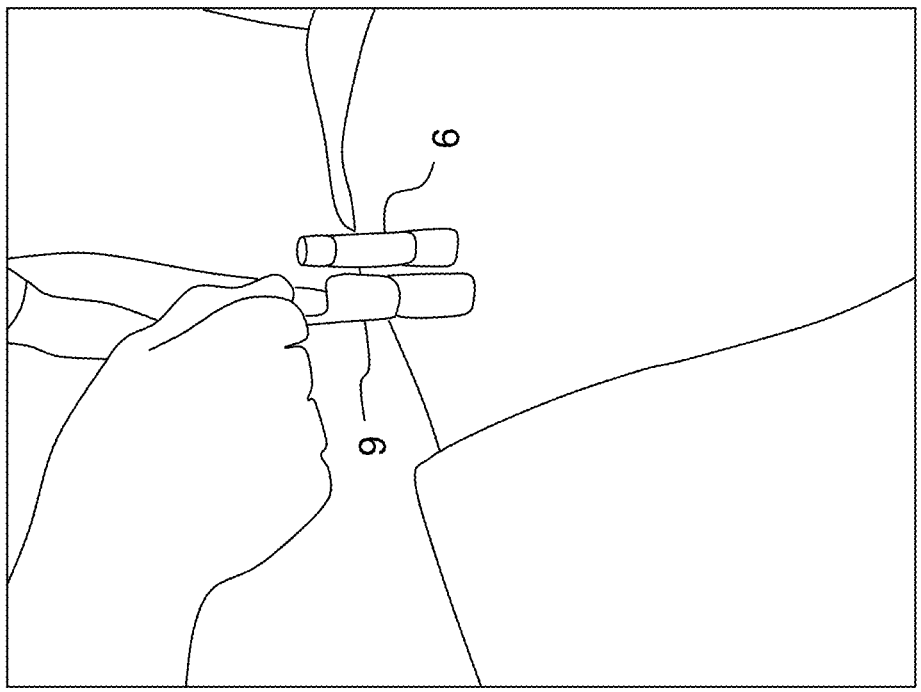
Figure 26:
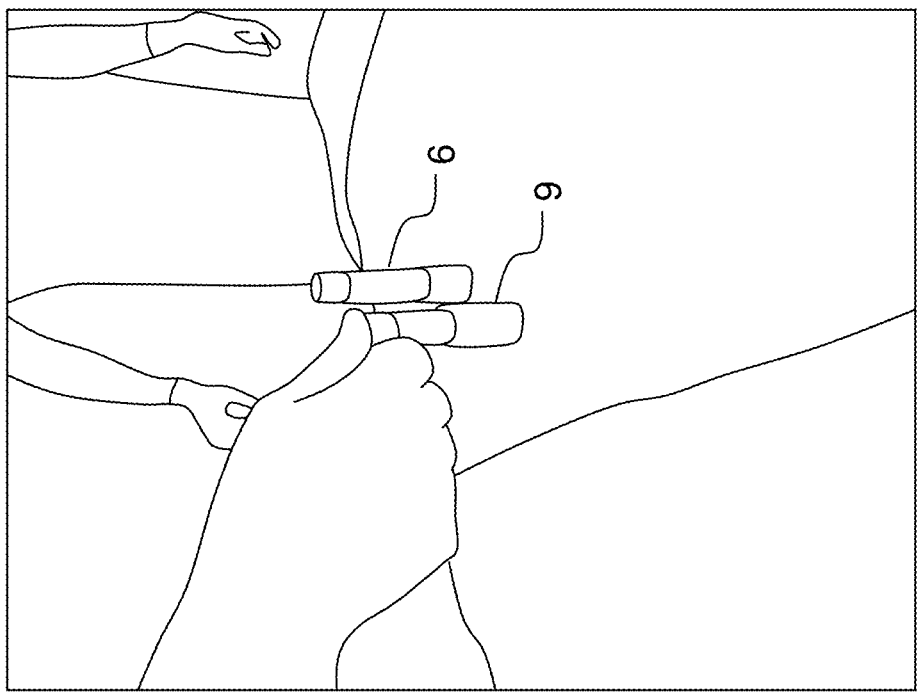
Figure 28:
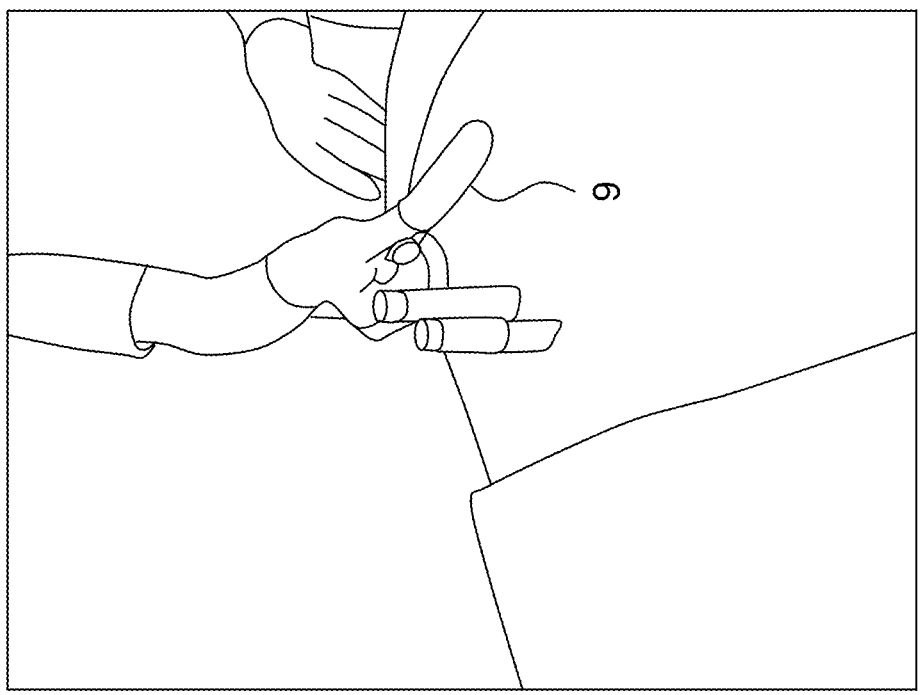

The tissue dilatation sleeves 9 are removed (FIGS. 26 to 28).

Figure 30:
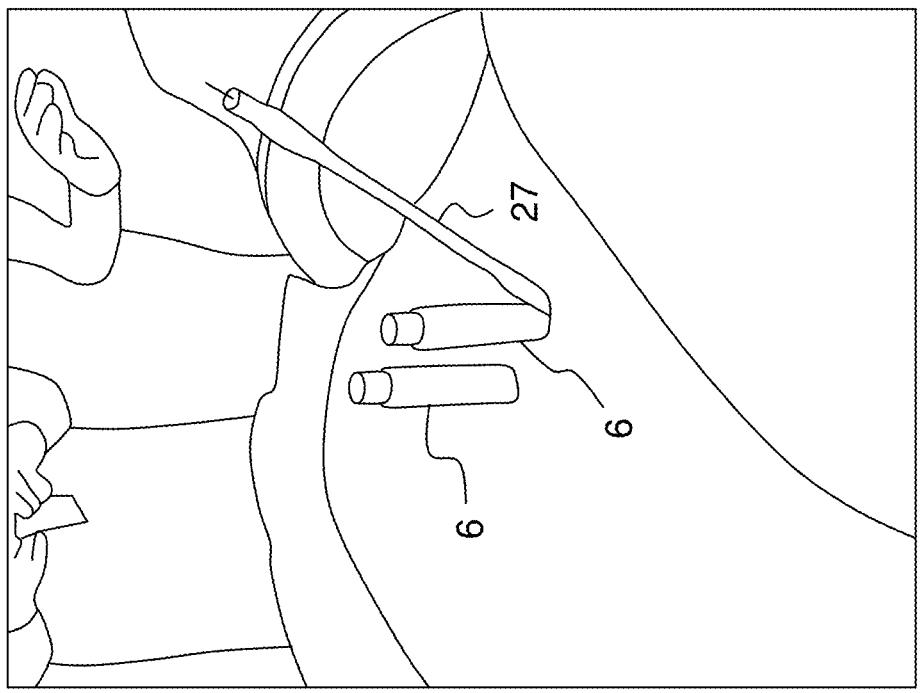
Figure 29:
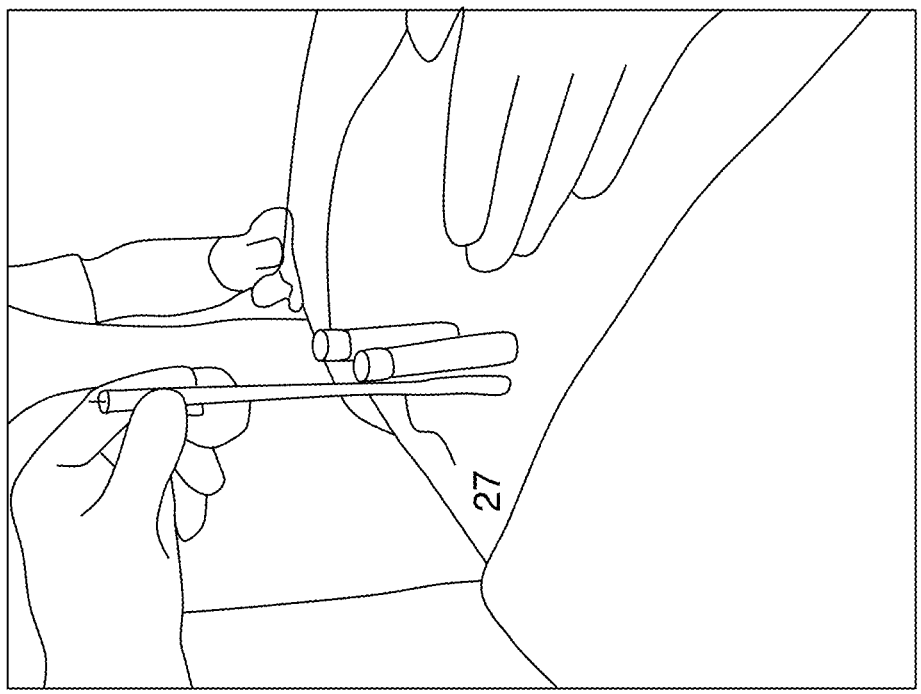

A rod inserting instrument 27 with a rod 7 at its end is transversally crossing the tissue (FIGS. 29 and 30).

Figure 32:
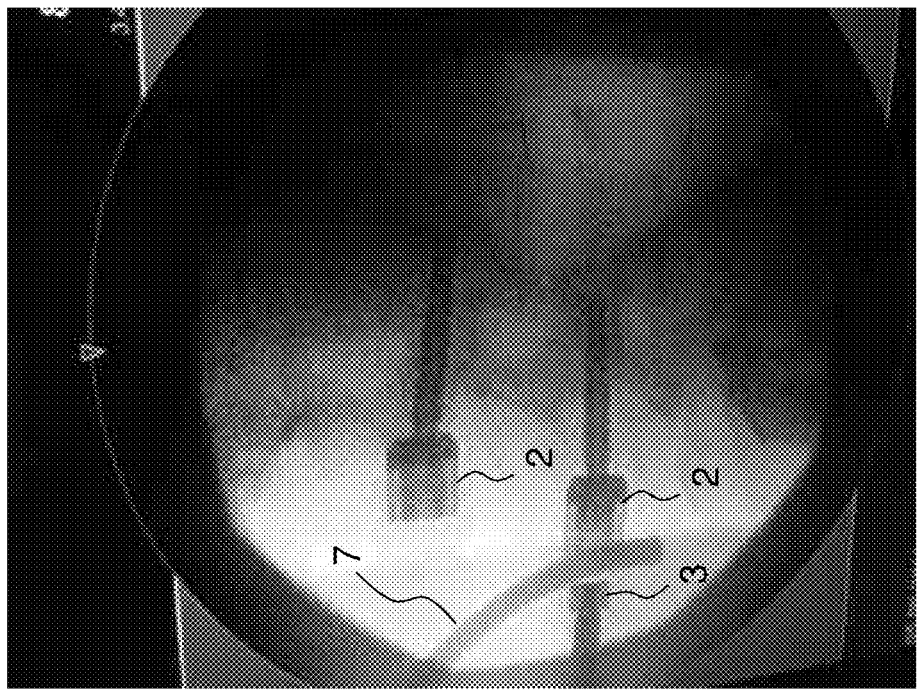
Figure 31:
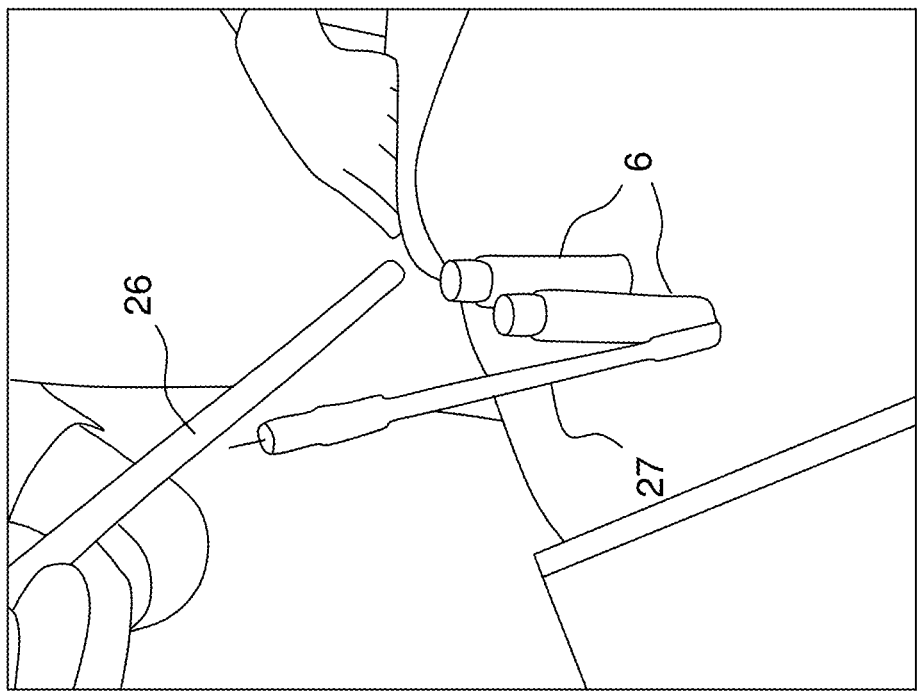
Figure 34:
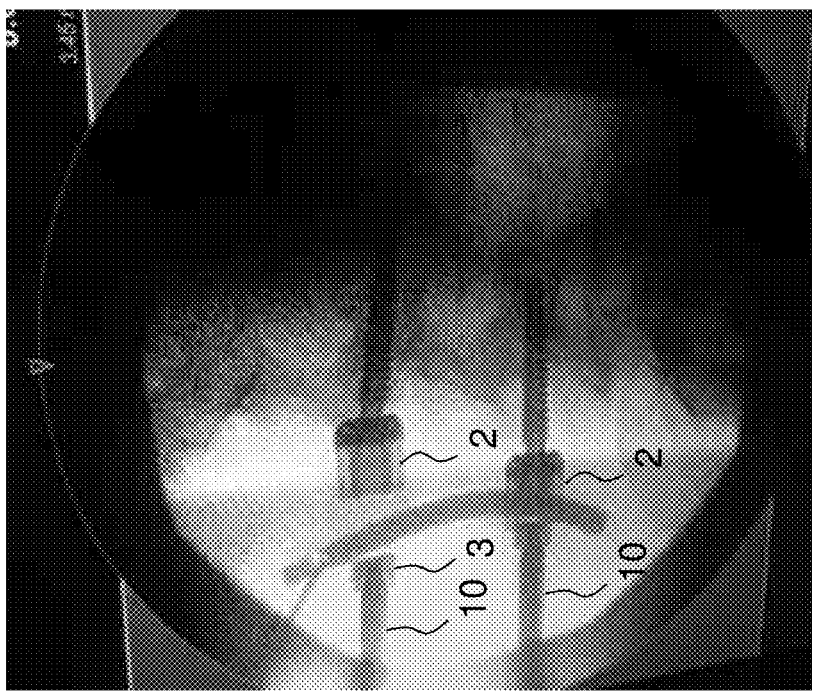
Figure 33:
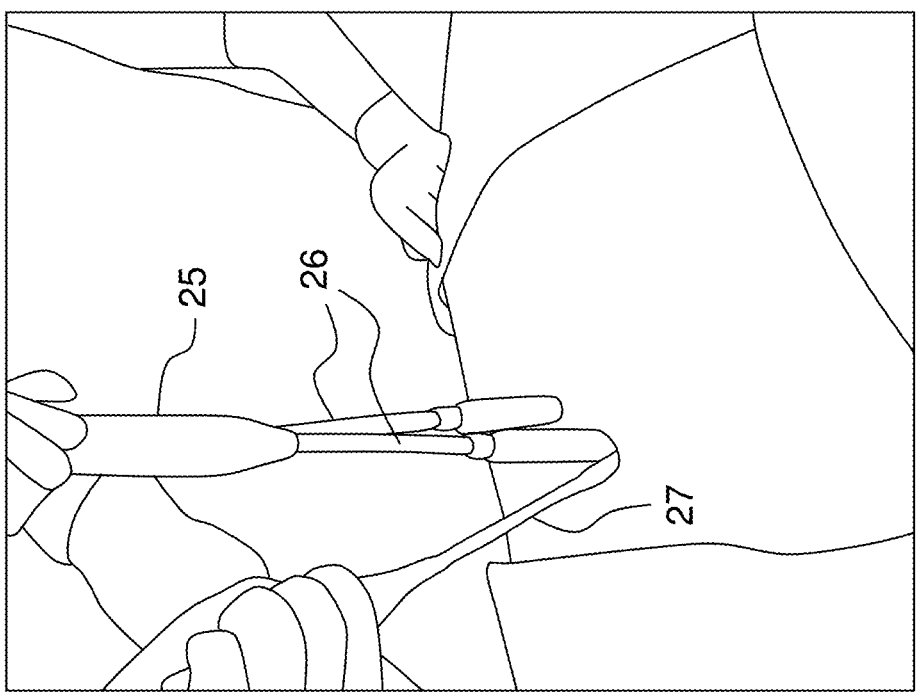
Figure 36:
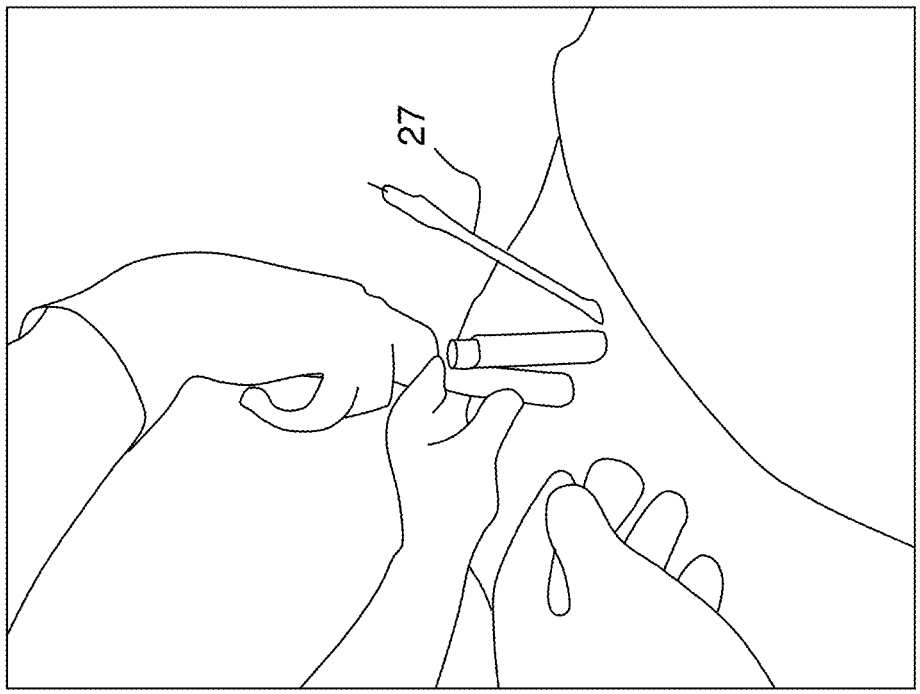
Figure 35:
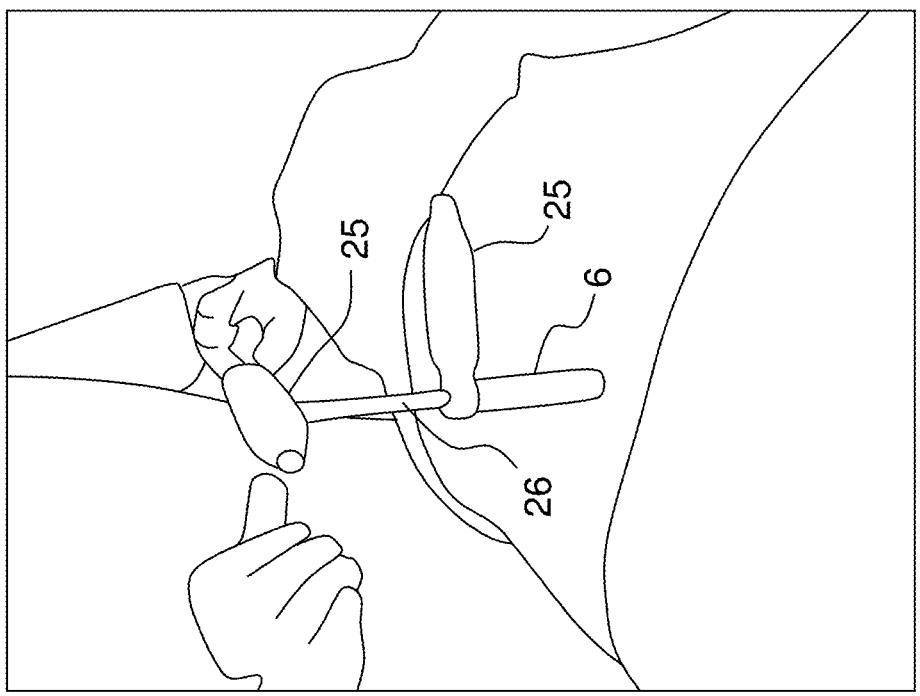

The rod 7 is positioned above the screw head 2 (FIG. 32) and the multi-use instrument 26 is introduced within the screw extender 6, to such an extent that the set screw 3 is positioned above the rod 7, in line with the screw head 2 (FIGS. 31 and 32).

FIGS. 33 to 36 show the rod placement within the screw heads 2 and the fixation of the set screw 3 within the screw head 2.

Figure 38:
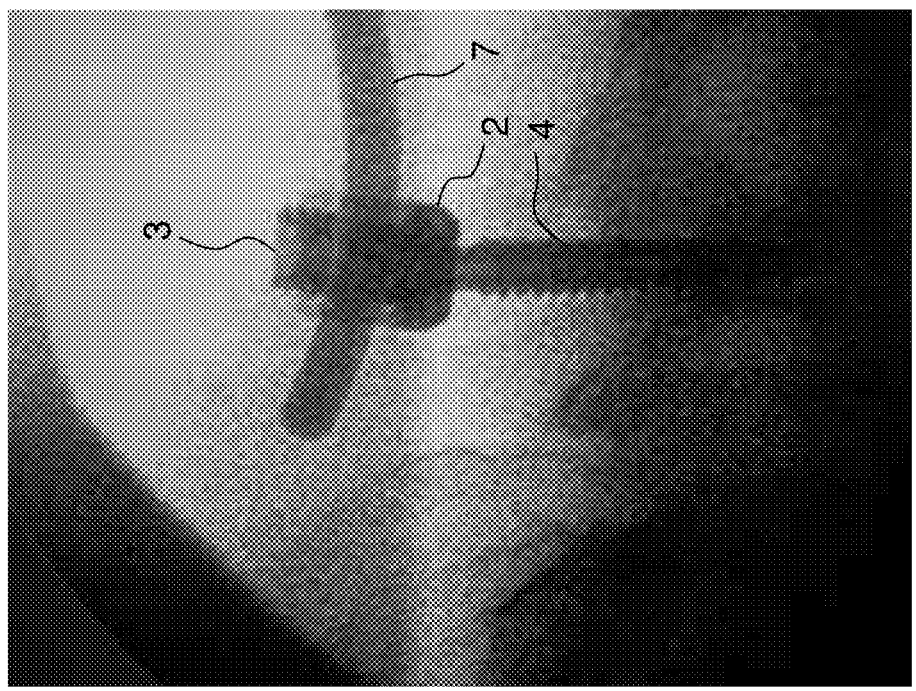
Figure 37:
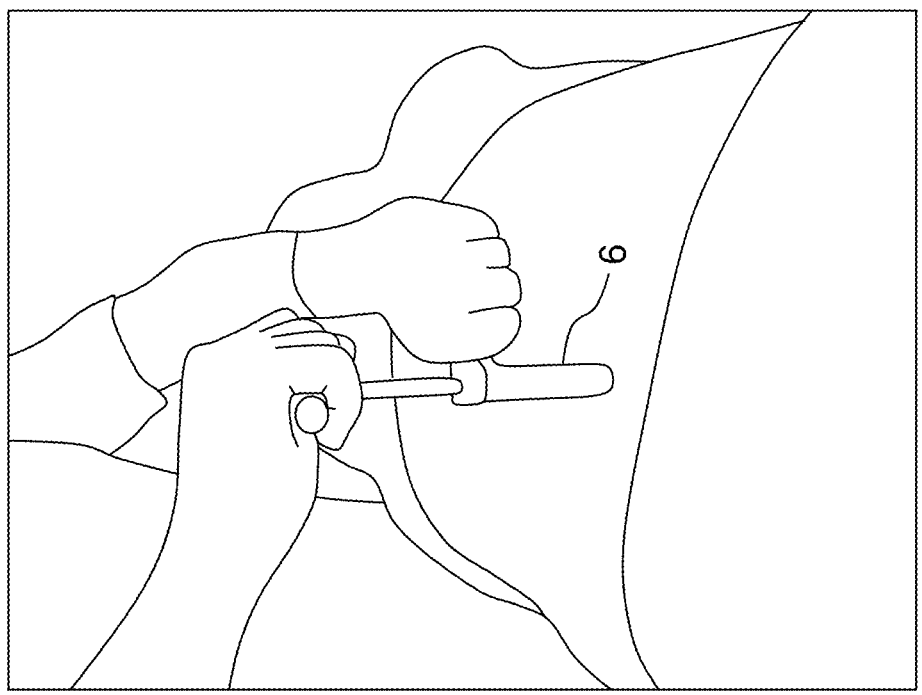

FIGS. 37 and 38 illustrate the screw release from the screw extender 6 and the screw 1, the rod 7 and the screw set 3 in their definitive location.

The invention is of course not limited to those illustrated examples.

The screw extender according to the invention may be used with mono-axial, poly-axial or lockable poly-axial screws.

The invention claimed is:

1. An orthopedic implant kit comprising:
a screw extender for holding a screw;
a tissue dilatation sleeve for removable attachment to the screw extender, the tissue dilatation sleeve comprising:
a cylindrical part for surrounding the screw extender,
a flexible conical part attached to one end of the cylindrical part, the flexible conical part tapering in direction away from the cylindrical part, and
a handle attached to the other end of the cylindrical part for manually pulling and removing the tissue dilatation sleeve from the screw extender along a longitudinal axis of the screw extender,
wherein the cylindrical part includes a first opening at said other end of the cylindrical part and the screw extender extends through the first opening, and
the handle includes a second opening configured to receive a finger of a user inside the second opening to grip the handle inside the second opening by said finger to pull and remove the tissue dilatation sleeve from the screw extender along a longitudinal axis of the screw extender, the second opening being perpendicular to the first opening when the tissue dilatation sleeve is assembled to the screw extender.

2. The orthopedic implant kit according to claim 1, wherein the flexible conical part is made of a plurality of longitudinal flexible blades having each a substantially triangular shape, adjacent flexible blades being separated from each other by a gap.

3. The orthopedic implant kit according to claim 1, wherein the flexible conical part is configured to cover the screw held by a distal part of the screw extender, when the tissue dilatation sleeve is attached to the screw extender.

4. The orthopedic implant kit according to claim 1, wherein the second opening is formed within a ring that is attached to the other end of the cylindrical part, the ring configured to engage with the finger of the user for pulling and removing the tissue dilatation sleeve from the screw extender along the longitudinal axis.

5. The orthopedic implant kit according to claim 2, wherein upon manually pulling and removing the tissue dilatation sleeve from the screw extender by the handle, the flexible blades of the conical part are configured to radially bend away from the screw extender, such that the tissue dilatation sleeve can be pulled and removed from the screw extender along the longitudinal axis.

6. The orthopedic implant kit according to claim 1, wherein the second opening passes fully through the handle.

7. The orthopedic implant kit according to claim 1, wherein the second opening extends laterally with respect to the screw extender to permit the screw extender to be located inside the first opening and outside the second opening.

8. The orthopedic implant kit according to claim 1, wherein said one end of the cylindrical part is located at a distal end of the tissue dilatation sleeve, and said other end of the cylindrical part is located at a proximal end of the tissue dilatation sleeve.

9. The orthopedic implant kit according to claim 1, wherein a longitudinal axis of the second opening of the handle is transverse to a longitudinal axis of the first opening of the cylindrical part.

\* \* \* \* \*